(12) United States Patent
Daly et al.

(10) Patent No.: US 9,427,538 B2
(45) Date of Patent: *Aug. 30, 2016

(54) MULTIPLE STAGE BLOWERS AND VOLUTES THEREFOR

(71) Applicant: ResMed Limited, Bella Vista, New South Wales (AU)

(72) Inventors: Geoffrey Daniel Daly, Brisbane (AU); Alexander Virr, Gosford (AU); Stephen Anthony Lea, Sydney (AU); Nicholas Jerome Reed, Sydney (AU)

(73) Assignee: ResMed Limited, Bella Vista (AU)

( * ) Notice: Subject to any disclaimer, the term of this patent is extended or adjusted under 35 U.S.C. 154(b) by 444 days.

This patent is subject to a terminal disclaimer.

(21) Appl. No.: 13/954,300

(22) Filed: Jul. 30, 2013

(65) Prior Publication Data

US 2014/0041663 A1 Feb. 13, 2014

Related U.S. Application Data

(63) Continuation of application No. 10/864,869, filed on Jun. 10, 2004, now Pat. No. 8,517,012, which is a continuation-in-part of application No. 10/360,757, filed on Dec. 10, 2001, now Pat. No. 6,910,483.

(60) Provisional application No. 60/477,358, filed on Jun. 11, 2003, provisional application No. 60/477,063, filed on Jun. 10, 2003.

(51) Int. Cl.
 *A61M 16/10* (2006.01)
 *A61M 16/00* (2006.01)
 (Continued)

(52) U.S. Cl.
 CPC ..... *A61M 16/0066* (2013.01); *A61M 16/0057* (2013.01); *A61M 16/0069* (2014.02);
 (Continued)

(58) Field of Classification Search
 CPC .................. A61M 16/0057; A61M 16/0066; A61M 16/1075; A61M 16/1085; A61M 16/109; A61M 16/1095; A61M 16/16; A61M 16/20; A61M 16/202; A61M 2205/21; A62B 23/00; A62B 9/003; A62B 9/02; B01D 47/021; B41J 29/13; F01C 21/10; F02M 23/14; F02M 25/00; F04B 49/24; F04C 11/008; F04C 15/0026; F04C 15/0069; F04C 2/086; F04C 2/16; F04C 2/18; F04D 25/082; F04D 29/626; F16K 11/052; F16M 1/00; F24F 7/065; F25D 15/00; G01F 1/363; G01F 1/40; G05D 7/0173; G06F 1/20; G11B 17/038; G11B 23/505; G11B 23/507; G11B 33/1446; G11B 5/4806; H02K 5/24
 USPC ............ 128/200.11, 200.13, 200.14, 200.16, 128/203.12, 203.16, 203.17, 203.26, 128/203.27, 204.14, 204.16, 204.17, 128/204.18, 204.23, 205.27
 See application file for complete search history.

(56) References Cited

U.S. PATENT DOCUMENTS

RE19,826 E    1/1936  Aisenstein
2,220,669 A  11/1940  Allen
(Continued)

FOREIGN PATENT DOCUMENTS

DE       275 612 C    6/1914
DE       30 05 094    8/1981
(Continued)

OTHER PUBLICATIONS

J. H. Emerson Co., Cough Assist, "Non-Invasive Removal of Bronchial Secretions," Date unknown but prior to the date of this application, 2 pgs.

(Continued)

*Primary Examiner* — Annette Dixon
(74) *Attorney, Agent, or Firm* — Nixon & Vanderhye P.C.

(57) ABSTRACT

A multiple stage variable speed blower for Continuous Positive Airway Pressure (CPAP) ventilation of patients includes two impellers in the gas flow path that cooperatively pressurize gas to desired pressure and flow characteristics. Thus, the multiple stage blower can provide faster pressure response and desired flow characteristics over a narrower range of motor speeds, resulting in greater reliability and less acoustic noise.

28 Claims, 24 Drawing Sheets

(51) Int. Cl.
    *F04D 17/12* (2006.01)
    *F04D 25/16* (2006.01)
    *F04D 29/28* (2006.01)

(52) U.S. Cl.
    CPC .......... *A61M16/105* (2013.01); *F04D 17/122* (2013.01); *F04D 25/166* (2013.01); *F04D 29/284* (2013.01); *A61M 16/107* (2014.02); *A61M 2205/42* (2013.01)

(56) References Cited

U.S. PATENT DOCUMENTS

| | | |
|---|---|---|
| 2,603,157 A | 7/1952 | Conery |
| 2,793,506 A | 6/1957 | Moody |
| 2,945,619 A | 7/1960 | McLure |
| 3,171,353 A | 3/1965 | McMahan |
| 3,612,710 A | 10/1971 | Mount |
| 3,619,851 A * | 11/1971 | Bolzan, Jr. ............... A47L 5/362 15/323 |
| 3,620,638 A | 11/1971 | Kaye et al. |
| 3,651,536 A * | 3/1972 | Bolzan, Jr. ............ A47L 9/0036 15/323 |
| 4,037,994 A | 7/1977 | Bird |
| 4,105,372 A | 8/1978 | Mishina et al. |
| 4,171,190 A | 10/1979 | Hudson |
| 4,229,142 A | 10/1980 | Le Dall et al. |
| 4,502,481 A | 3/1985 | Christian |
| 4,523,896 A | 6/1985 | Lhenry et al. |
| 4,576,616 A | 3/1986 | Mottram et al. |
| 4,725,904 A * | 2/1988 | Dalziel ............... G11B 33/1446 360/264.6 |
| 4,802,819 A | 2/1989 | Bevington |
| 4,929,149 A | 5/1990 | Greenspan |
| 4,946,348 A | 8/1990 | Yapp |
| 5,127,800 A | 7/1992 | Hyll et al. |
| 5,199,846 A | 4/1993 | Fukasaku et al. |
| 5,230,612 A * | 7/1993 | Murphy ................... F16M 1/00 248/638 |
| 5,389,037 A * | 2/1995 | Hale ........................ F24F 7/065 128/204.18 |
| 5,391,063 A | 2/1995 | Hantle et al. |
| 5,487,378 A * | 1/1996 | Robertson ......... A61M 15/0065 128/200.14 |
| 5,573,088 A * | 11/1996 | Daniels ............. B60G 17/0157 188/267 |
| 5,702,234 A * | 12/1997 | Pieters .................... F01C 21/10 417/420 |
| 5,888,053 A | 3/1999 | Kobayashi et al. |
| 5,937,475 A * | 8/1999 | Kasen ....................... A47L 5/30 15/320 |
| 6,109,865 A | 8/2000 | Ishikawa |
| 6,158,978 A | 12/2000 | Norbury, Jr. |
| 6,210,116 B1 | 4/2001 | Kuczaj et al. |
| 6,213,119 B1 | 4/2001 | Brydon et al. |
| 6,216,691 B1 | 4/2001 | Kenyon et al. |
| 6,257,171 B1 | 7/2001 | Rivard |
| 6,340,288 B1 | 1/2002 | Hulkkonen et al. |
| 6,349,724 B1 | 2/2002 | Burton et al. |
| 6,397,841 B1 | 6/2002 | Kenyon et al. |
| 6,435,180 B1 * | 8/2002 | Hewson ................ A61M 16/16 128/203.12 |
| 6,471,493 B2 | 10/2002 | Choi et al. |
| 6,514,053 B2 | 2/2003 | Takura et al. |
| 6,622,724 B1 | 9/2003 | Truitt et al. |
| 6,672,300 B1 | 1/2004 | Grant |
| 6,837,260 B1 | 1/2005 | Kuehn |
| 6,896,478 B2 | 5/2005 | Botros et al. |
| 6,910,483 B2 | 6/2005 | Daly et al. |
| 8,006,691 B2 * | 8/2011 | Kenyon ............ A61M 16/0051 122/4 R |
| 8,517,012 B2 * | 8/2013 | Daly ................. A61M 16/0057 128/204.18 |
| 2002/0056453 A1 | 5/2002 | Klopp et al. |
| 2002/0159897 A1 | 10/2002 | Kegg et al. |
| 2003/0084900 A1 | 5/2003 | Leclerc et al. |
| 2003/0168064 A1 | 9/2003 | Daly et al. |
| 2004/0035422 A1 | 2/2004 | Truitt et al. |
| 2005/0005937 A1 | 1/2005 | Farrugia et al. |
| 2005/0103339 A1 | 5/2005 | Daly et al. |
| 2005/0217673 A1 | 10/2005 | Daly et al. |
| 2007/0036662 A1 | 2/2007 | Pesola et al. |
| 2012/0266887 A1 | 10/2012 | Daly et al. |

FOREIGN PATENT DOCUMENTS

| | | |
|---|---|---|
| DE | 41 11 138 A1 | 10/1992 |
| EP | 0 290 062 A2 | 11/1988 |
| EP | 0 471 089 A1 | 2/1992 |
| EP | 1318307 | 6/2003 |
| JP | 38-15973 | 8/1938 |
| JP | 40-35414 | 12/1940 |
| JP | 53-104402 U | 8/1978 |
| JP | 64-80799 A | 3/1989 |
| JP | 3-47500 A | 2/1991 |
| JP | 3-253794 A | 11/1991 |
| JP | 4-159500 A | 6/1992 |
| JP | 4-353299 A | 12/1992 |
| JP | 5-89887 U | 12/1993 |
| JP | 7-145795 A | 6/1995 |
| JP | 7-275362 A | 10/1995 |
| JP | 8-93691 A | 4/1996 |
| JP | 11-148119 A | 6/1999 |
| JP | 2002-106495 A | 4/2002 |
| JP | 2002-206498 A | 7/2002 |
| JP | 2002-537006 A | 11/2002 |
| WO | WO 98/31937 A | 7/1998 |
| WO | WO 98/33433 | 8/1998 |
| WO | WO 99/13932 A | 3/1999 |
| WO | WO 99/22794 | 5/1999 |
| WO | WO 99/64747 | 12/1999 |
| WO | WO 00/42324 A | 7/2000 |
| WO | WO 02/02169 A1 | 1/2002 |
| WO | WO 03/040567 A1 | 5/2003 |

OTHER PUBLICATIONS

International Search Report for PCT/AU2004/000771, Mailed Aug. 23, 2004, 6 pages.
Examiner's First Report Mailed May 30, 2011 in Australian Application No. 2011202113 (2 pages).
Supplementary European Search Report Mailed Jun. 17, 2011 in European Application No. 04736483.1 (3 pages).
Appeal Decision mailed Oct. 18, 2011 in Japanese Appln. No. 2006-515536 (Appeal No. 2011-1175), with English Translation (17 pages).
Communication mailed Apr. 27, 2012 in European Application No. 04 736 483.1 (5 pages).
Notice of Reasons for Rejection mailed Jul. 31, 2012 in Japanese Application No. 2011-007878, with English Translation (9 pages).
Notice of Reasons for Rejection mailed Apr. 23, 2013 in Japanese Application No. 2011-007878, with English Translation (9 pages).
Notice of Reasons for Rejection mailed Apr. 23, 2013 in Japanese Application No. 2012-039850, with English Translation (7 pages).
Requisition by the Examiner mailed Apr. 26, 2013 in Canadian Application No. 2,528,384.

* cited by examiner

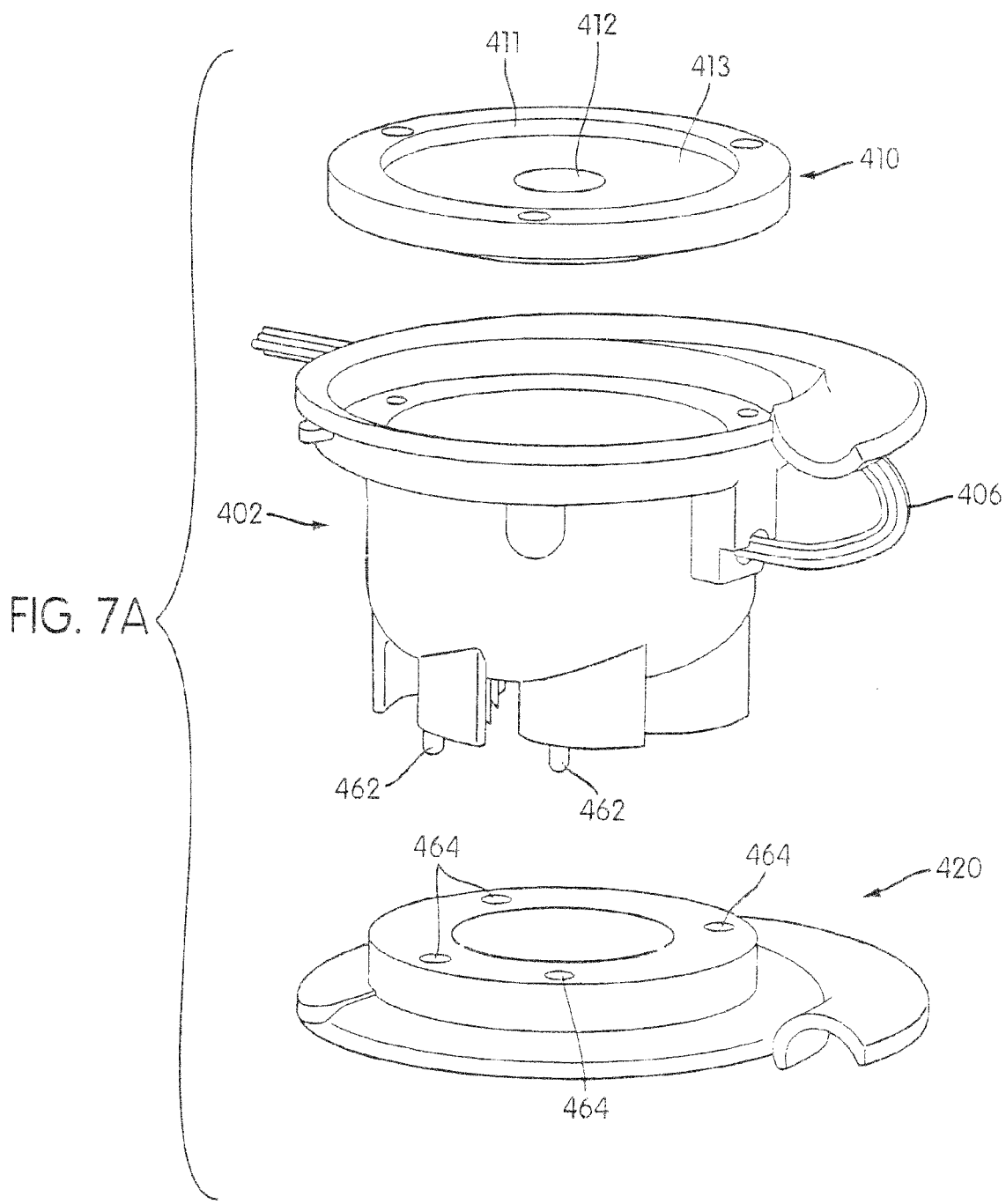

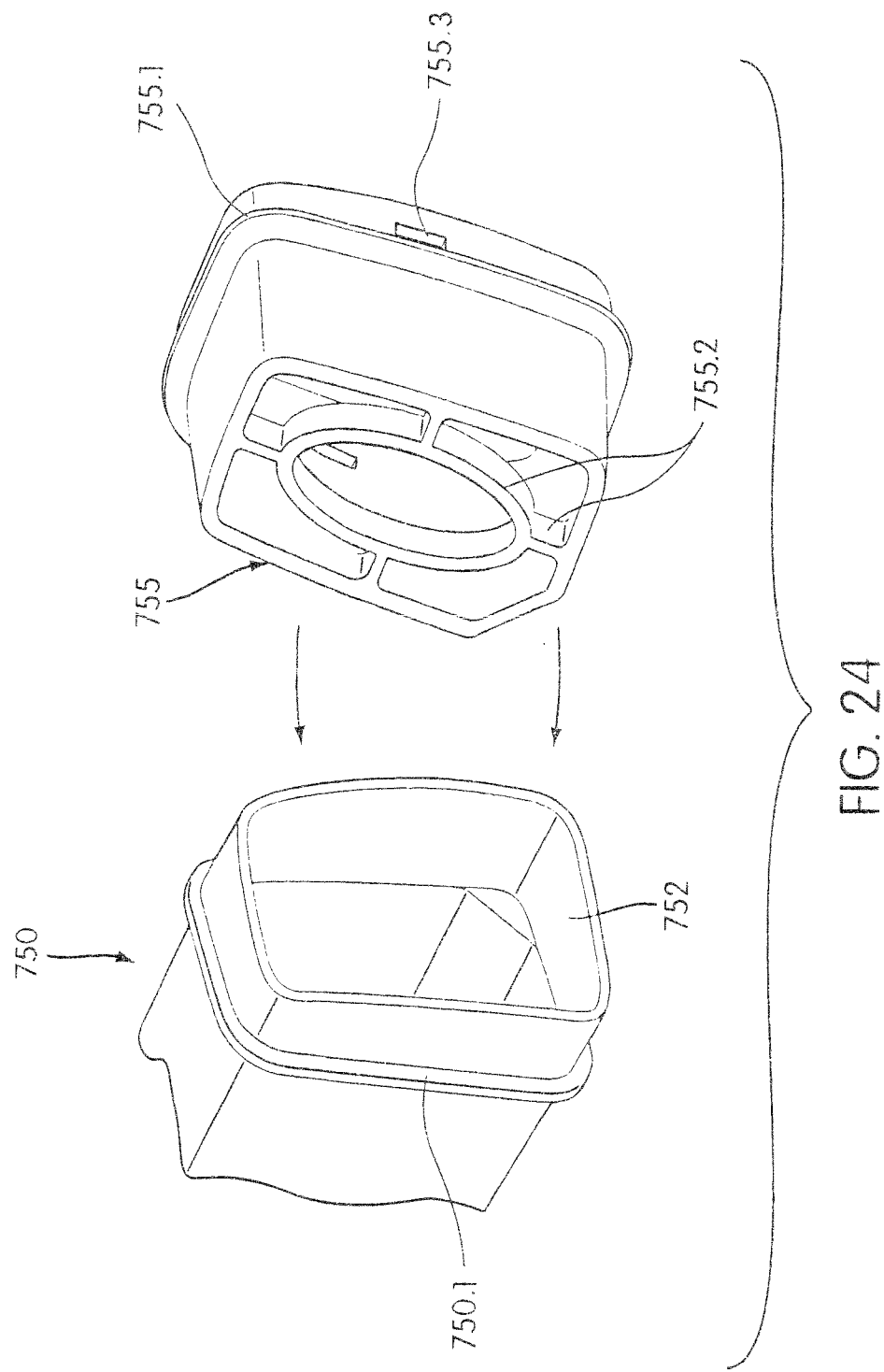

MULTIPLE STAGE BLOWERS AND VOLUTES THEREFOR

CROSS-REFERENCES TO RELATED APPLICATIONS

This application is a continuation of U.S. application Ser. No. 10/864,869, filed Jun. 10, 2004, now U.S. Pat. No. 8,517,012, which is continuation-in-part of U.S. application Ser. No. 10/360,757, which was filed on Dec. 10, 2001, now U.S. Pat. No. 6,910,483, and is hereby incorporated in its entirety by reference. This application also claims the benefit of U.S. Provisional Application No. 60/477,063, filed Jun. 10, 2003, and U.S. Provisional Application No. 60/477,358 filed Jun. 11, 2003, each of which is incorporated herein by reference in its entirety.

BACKGROUND OF THE INVENTION

1. Field of the Invention

The present invention relates to an apparatus for supplying breathable gas to a human, used in, for example, Continuous Positive Airway Pressure (CPAP) treatment of Obstructive Sleep Apnea (OSA), other respiratory diseases and disorders such as emphysema, or the application of assisted ventilation.

2. Description of Related Art

CPAP treatment of OSA, a form of Noninvasive Positive Pressure Ventilation (NIPPY), involves the delivery of a pressurized breathable gas, usually air, to a patient's airways using a conduit and mask. Gas pressures employed for CPAP can range, e.g., from 4 cm $H_2O$ to 28 cm $H_2O$, at flow rates of up to 180 L/min (measured at the mask), depending on patient requirements. The pressurized gas acts as a pneumatic splint for the patient's airway, preventing airway collapse, especially during the inspiratory phase of respiration.

Typically, the pressure at which a patient is ventilated during CPAP is varied according to the phase of the patient's breathing cycle. For example, the ventilation apparatus may be pre-set, e.g., using control algorithms, to deliver two pressures, an inspiratory positive airway pressure (IPAP) during the inspiration phase of the respiratory cycle, and an expiratory positive airway pressure (EPAP) during the expiration phase of the respiratory cycle. An ideal system for CPAP is able to switch between IPAP and EPAP pressures quickly, efficiently, and quietly, while providing maximum pressure support to the patient during the early part of the inspiratory phase.

In a traditional CPAP system, the air supply to the patient is pressurized by a blower having a single impeller. The impeller is enclosed in a volute, or housing, in which the entering gas is trapped while pressurized by the spinning impeller. The pressurized gas gradually leaves the volute and travels to the patient's mask, e.g., via an air delivery path typically including an air delivery tube.

There are currently two common ways in which the blower and impeller can be configured to produce the two different pressures, IPAP and EPAP, that are required in an ideal CPAP system. A first method is to set the motor/impeller to produce a constant high pressure and then employ a diverter valve arrangement that modulates the high pressure to achieve the required IPAP and EPAP pressures. CPAP systems according to the first method are called single-speed bi-level systems with diverters. A second method is to accelerate the motor that drives the impeller to directly produce IPAP and EPAP pressures. CPAP systems according to the second method are called variable-speed hi-level systems.

Variable-speed bi-level CPAP systems have a number of particular disadvantages. A first disadvantage is that in order to switch rapidly between IPAP and EPAP, the impeller must be accelerated and decelerated rapidly. This causes excessive stress on the impeller, motor, and bearings. However, if the impeller is accelerated slowly, the pressure rise may be unsatisfactorily slow, and thus, the patient may not receive adequate treatment.

Rapid acceleration and deceleration of the motor and impeller also result in excessive heat generation and undesirable acoustic noise. ("Undesirable" acoustic noise, as the term is used here, refers to acoustic noise that is overly loud, as well as acoustic noise which occurs at a frequency that is irritating to the user, regardless of its volume.) In addition, design engineers are often forced to make a compromise, sacrificing optimal pressure and flow characteristics in favor of achieving a desired peak pressure.

SUMMARY OF THE INVENTION

The present invention, in one aspect, relates to variable speed blowers providing faster pressure rise time with increased reliability and less acoustic noise. Blowers according to an embodiment of the present invention comprise a gas flow path between a gas inlet and a gas outlet, a motor, and an impeller assembly.

Preferably, the impeller assembly may include a shaft in communication with the motor for rotational motion about a first axis and first and second impellers coupled, e.g., fixedly secured, to the shaft. The impellers are placed in fluid communication with one another by the gas flow path such that both impellers are disposed between the gas inlet and the gas outlet to cooperatively pressurize gas flowing from the gas inlet to the gas outlet.

In one embodiment, the impellers are disposed in series between the gas inlet and the gas outlet. The blower may also comprise a housing, portions of the housing being disposed around each of the first and second impellers. In particular, the housing may include first and second volutes, the first volute containing gas flow around the first impeller and the second volute containing gas flow around the second impeller. The gas inlet may be located in the first volute and the gas outlet may be located in the second volute.

The impellers may be arranged such that they are vertically spaced from one another along the first axis. In particular, they may be disposed at opposite ends, respectively, of the blower housing.

A blower according to an embodiment of the present invention may have varying configurations. In one embodiment, the two impellers are designed to rotate in the same direction. In another embodiment, the two impellers are designed to rotate in opposite directions.

Another aspect of the invention relates to an in-plane transitional scroll volute for use in either a double- or single-ended blower. The in-plane transitional scroll volute gradually directs pressurized air away from a spinning impeller.

A further aspect of the invention involves a method and apparatus for minimizing blower-induced turbulence presented to a flow meter for measuring the air flow. In one embodiment, the flow meter is positioned upstream from the blower.

In yet another aspect, a blower has a motor provided with opposed first and second shafts. First and second stage impellers are provided to the first and second shafts, respectfully. An inner casing supports the motor and an outer casing supports the inner casing. In addition, a substantially annular channel is provided between the inner and outer casings. In operation, gas is directed from the first stage impeller towards the second stage impeller via the substantially annular channel.

Additional aspects, advantages and features of the present invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of the stated aspects, advantages and features make up the inventions disclosed in this application.

BRIEF DESCRIPTION OF THE DRAWINGS

Various exemplary embodiments will be described with reference to the following drawings, in which like reference characters represent like features, wherein:

FIG. 7A is a view of the press-fit connection between the motor and the contoured plate in FIG. 7;

FIG. 24 is a perspective view of a filter retainer for the enclosure of FIG. 14.

DETAILED DESCRIPTION OF PREFERRED EMBODIMENTS

Figure 1:
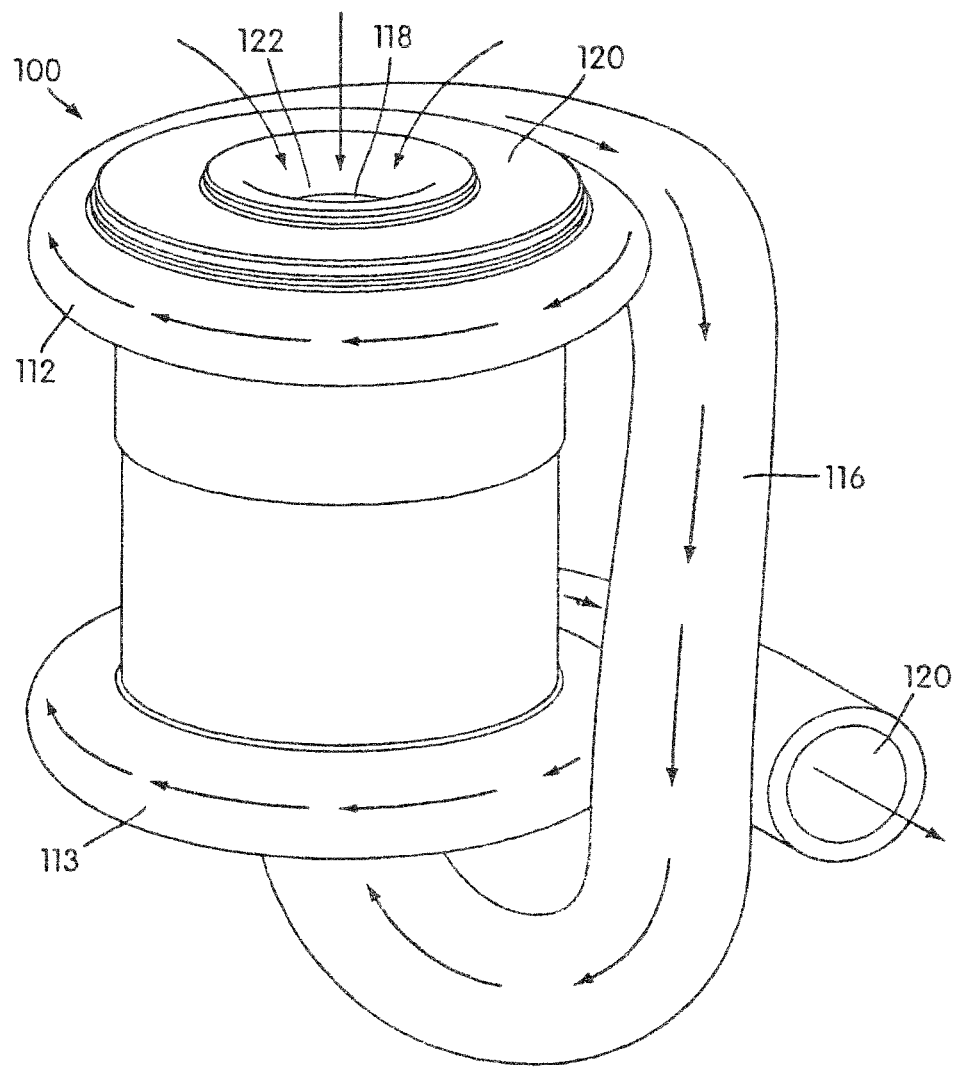
FIG. 1 is a perspective view of a double-ended blower according to a first embodiment of the present invention.

FIG. 1 is a perspective view of a double-ended blower 100 according to a first embodiment of the present invention. Blower 100 has a generally cylindrical shape with impeller housings, or volutes 112, 113, disposed at each end. Thus, blower 100 accommodates two impellers 114, 115, which are best seen in the cutaway perspective view of FIG. 2.

Figure 2:
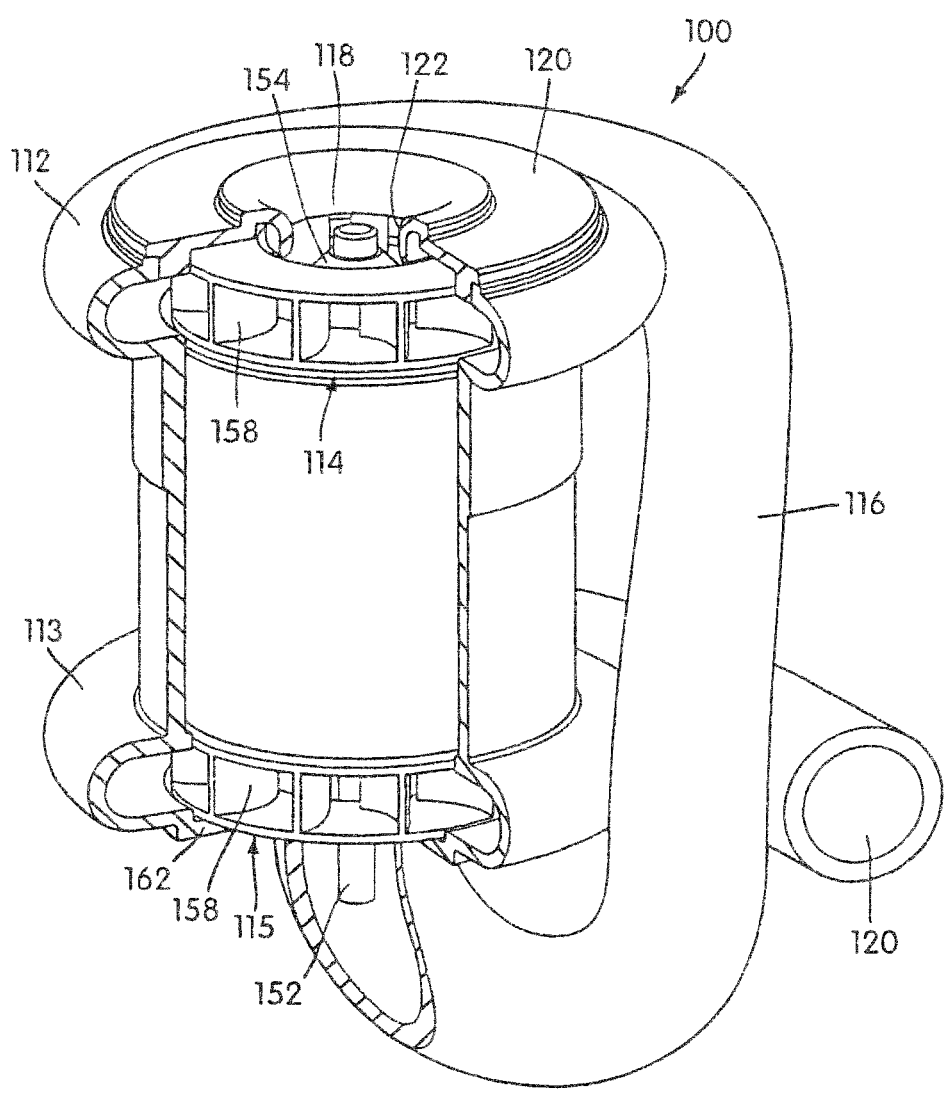
FIG. 2 is a partially sectional perspective view of the double-ended blower of FIG. 1.

As shown in FIGS. 1 and 2, the two impellers 114, 115 are placed in fluid communication with one another by an airpath 116. The airpath 116 of blower 100 is comprised of piping that extends from the first volute 112 to the second volute 113, the terminal ends of the airpath 116 being contoured around, and gradually fusing with, the body of blower 100 proximate to the volutes 112, 113 to form a single, integral structure. The airpath 116 may be comprised of substantially rigid piping that is, e.g., integrally molded with the other components of the blower 100, or it may be separately provided and joined to the blower 100 at each volute 112, 113.

Blower 100 has a single air intake 118 positioned such that air, or another suitable gas, flows directly into the first volute 112 and can be drawn in by the turning impeller 114 inside the first volute 112. Once drawn into the air intake 118, the air is circulated and pressurized by the motion of the impeller 114 before gradually exiting the volute 112 and entering the airpath 116. Once in the airpath 116, the air travels to the second volute 113, where it is further circulated and pressurized by the impeller 115 of the second volute 113 before exiting the blower 100 through the outflow conduit 120. The path of the air in blower 100 is indicated by the arrows in FIG. 1. As shown, in blower 100, air from the first volute 112 travels along a relatively straight section of the airpath 116 and enters the second volute 113 through an intake cavity just above the second volute 113 (not shown in FIG. 1).

Blower 100 could have, e.g., two air intakes 118, one for each volute 112, 113, if the impellers 114, 115 are designed to work in parallel, rather than in series. This type of parallel impeller arrangement may be beneficial if installed in a low-pressure CPAP device requiring high flow rates.

The design of the airpath 116 can affect the overall performance of the blower 100. In general, several design considerations influence the design of an airpath for use in blowers according to the present invention. First, airpaths to be used in blowers according to one embodiment of the present invention are most advantageously configured to provide low flow resistance, because low flow resistance in the airpath minimizes the pressure drop between the two volutes 112, 113 in the blower. Second, airpaths according to one embodiment of the present invention are best configured such that the air entering the second volute 113 enters from a direction for which the blades of the impeller 115 were designed. (As will be described in more detail below, the two impellers of a blower according to the present invention may be designed to spin in the same or different directions.) Third, airpaths according to one embodiment of the present invention are most advantageously of a compact design.

The design considerations set forth above may be embodied in an airpath having long, sweeping bends to minimize the pressure drop around the bends. It is also beneficial to have a relatively straight section after a bend in the airpath, because a relatively straight section after a bend aids in allowing the gas flow to become more fully developed before entering a volute. An appropriate length for a straight airpath section following a bend is, e.g., about three times the diameter of the airpath. The relatively straight section also aids in the flow entering the second volute 113 being axial, the flow orientation for which many impellers are designed. If additional flow shaping is desired, stator vanes or other similar flow directing structures may be added to the blower, however, stator vanes may be costly in terms of flow impedance and pressure drops.

In view of the three major airpath design considerations set forth above, the airpath 116 of the embodiment depicted in FIG. 1 has a long, relatively straight section because the relatively straight section is one of the shortest possible paths between the two volutes 112, 113. Those skilled in the art will realize that the airpath 116 need not be straight at all.

Blowers according to the invention may be designed manually, using prototypes and experimental measurements of air flows and pressures in those prototypes to optimize the design of the airpath 116 and other components. Alternatively, they may be designed, either as a whole or in part, by using computational fluid dynamics computer simulation programs. A variety of computational fluid dynamics programs are known in the art. Computational fluid dynamics programs particularly suited for the design of blowers according to the invention include, e.g., FLOWORKS (NIKA GmbH, Sottrum, Germany), ANSYS/FLOTRAN (Ansys, Inc., Canonsburg, Pa., USA), and CFX (AEA Technology Engineering Software, Inc., El Dorado Hills, Calif., USA). Such simulation programs give the user the ability to see the effects of airpath design changes on a simulated gas flow.

Many different types of configurations for the two volutes 112, 113 and airpath 116 are possible in a double-ended blower according to the present invention. In general, each volute is designed to retain the gas around the impeller for a short period of time, and to permit a gradual exit of gas into the airpath. The exact configuration of the airpath may depend on many factors, including the configuration of the volutes and the "handedness," or direction of airflow, around each impeller.

The design of the volutes is an art unto itself, as improperly designed volutes may cause a noise, or may interfere with the generation of the desired pressure and flow characteristics. The computational fluid dynamics computer programs described above may also be useful in designing the volutes, although the number of variables involved in volute design usually precludes the volute from being entirely computer-designed.

The type and direction of flow into each volute 112, 113 may influence the performance and noise characteristics of the impellers 114, 115. For this reason, a bell-shaped intake, rounded intake edges, stator vanes, or other flow directing/enhancing structures may be used at the entrance to either or both of the volutes 112, 113. However, the use of these types of flow enhancing/directing structure may increase the flow resistance.

Figure 3:
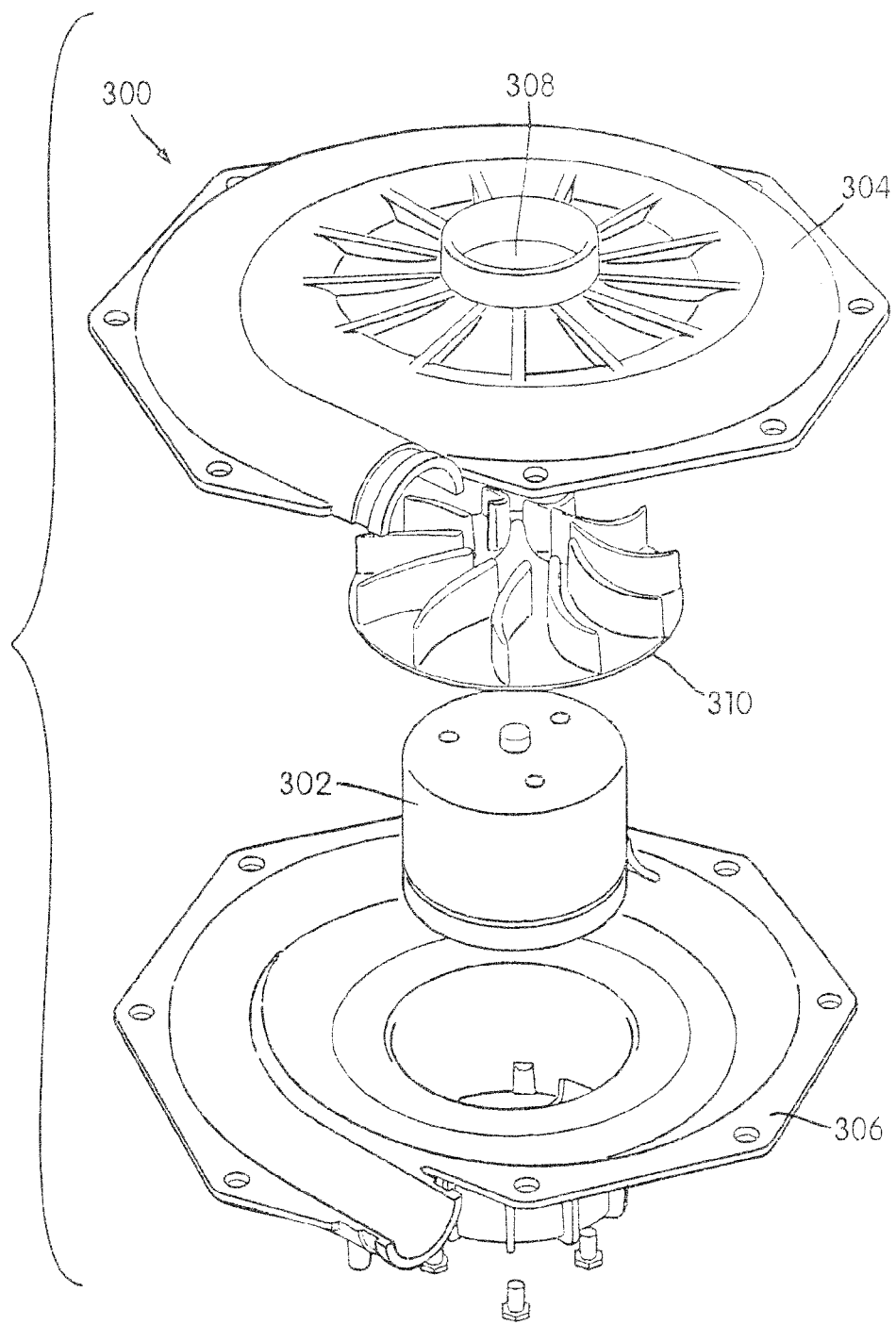
FIG. 3 is an exploded, perspective view of an in-plane transitional scroll volute suitable for use in blowers according to the present invention.

One common problem with volutes 112, 113 is that they may provide too abrupt of a transition into the airpath 116. An abrupt transition between the volute 112, 113 and the airpath 116 usually leaves a forked path or "lip" around the opening. When the impeller blades pass by this lip, a noise called "blade passing frequency" is created. Double-ended blowers according to the present invention are particularly suited for, e.g., use with volutes that are constructed to reduce the occurrence of "blade passing frequency" and other noise. See FIG. 3, for instance, which is a perspective view of an in-plane transitional scroll volute 300 suitable for use in a blower according to the present invention. Additionally, the volute 300 may be employed in any conventional blower apparatus. In the view of FIG. 3, the volute 300 is provided with its own motor 302, although it may be adapted for use in a double-ended blower having a single motor driving the impellers in two volutes. As shown, the volute 300 is comprised of two halves 304, 306, the two halves defining upper and lower portions of the volute 300, respectively. The air intake of the volute 308 is located at the center of the top half 304. The two halves 304, 306 define a path which slowly "peels" away from the air rotating with the impeller. In the path defined by the two halves, there is no sudden "lip" or "split" as in conventional volutes, therefore, "blade passing frequency" is reduced or eliminated entirely.

Alternatively, any common type of volute may be used, depending on the dimensions of the motor installed in the blower. Another suitable type of volute is the axial volute disclosed in U.S. patent application Ser. No. 09/600,738, filed on Jul. 21, 2000, the contents of which are hereby incorporated by reference herein in their entirety.

One design consideration for a double-ended blower according to the present invention is the "handedness," or direction of airflow, around each impeller. This "handedness" may be determined by the direction in which the impeller spins, or it may be determined by the orientation and configuration of the individual blades or vanes of the impeller. For example, one impeller may be spun or the blades oriented to drive the air in a clockwise direction, and the other impeller may be spun or the blades oriented to drive the air in a counterclockwise direction, resulting in a "opposing-handed" double-ended blower. Alternatively, both impellers could be driven in the same direction, resulting in a "same-handed" double-ended blower. Blower 100 of FIG. 1 is an example of an "opposite-handed" type of double-ended blower.

A "same-handed" blower is advantageous because the two impellers can be identical, reducing the part count and cost of the blower. However, it should be noted that a designer may choose to design a "same-handed" blower in which the two impellers are each designed and optimized separately for the air flow in their respective volutes.

An "opposing-handed" blower permits the designer to reduce the length of the shaft on which the impellers are mounted. This may increase the stability of the shaft itself, because it reduces the problems associated with having an imbalance on a long, cantilevered shaft rotating at high speed.

Figure 4:
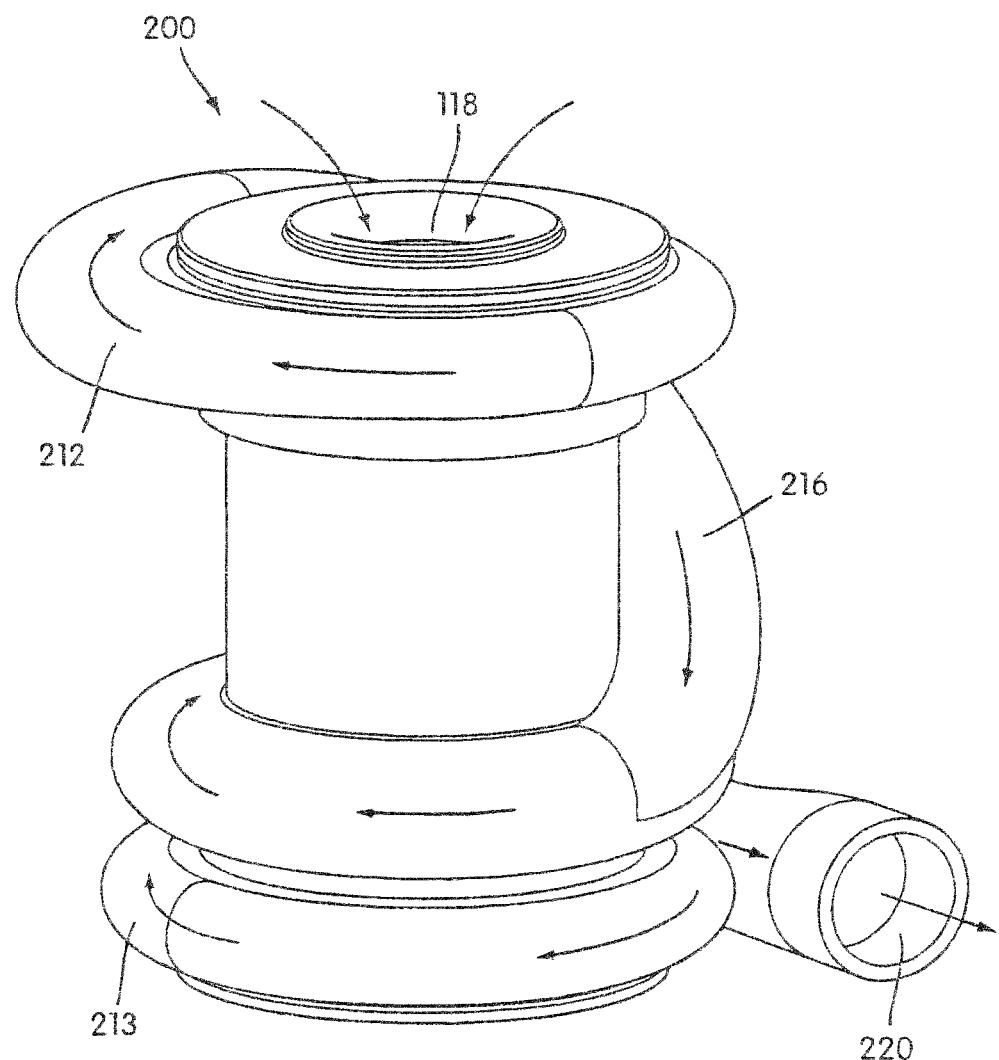
FIG. 4 is a perspective view of a double-ended blower according to a second embodiment of the present invention.
Figure 4A:
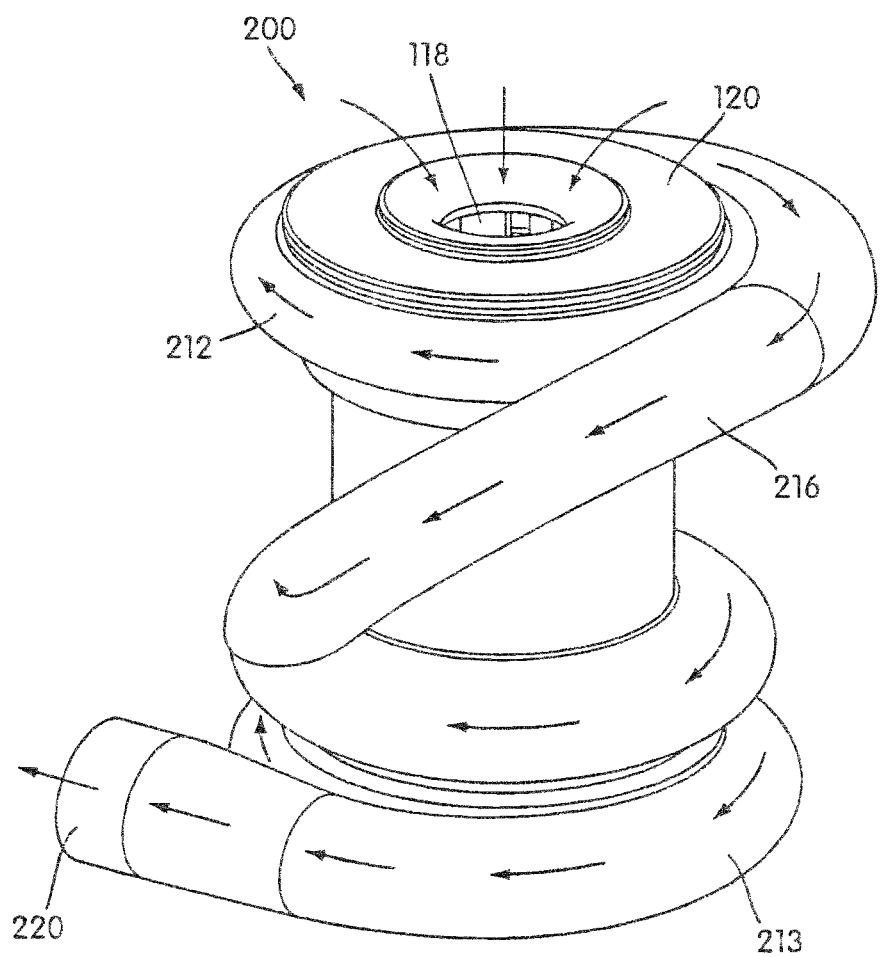
FIG. 4A is a rear perspective view of the double-ended blower of FIG. 4, illustrating the flow therethrough.
Figure 5:
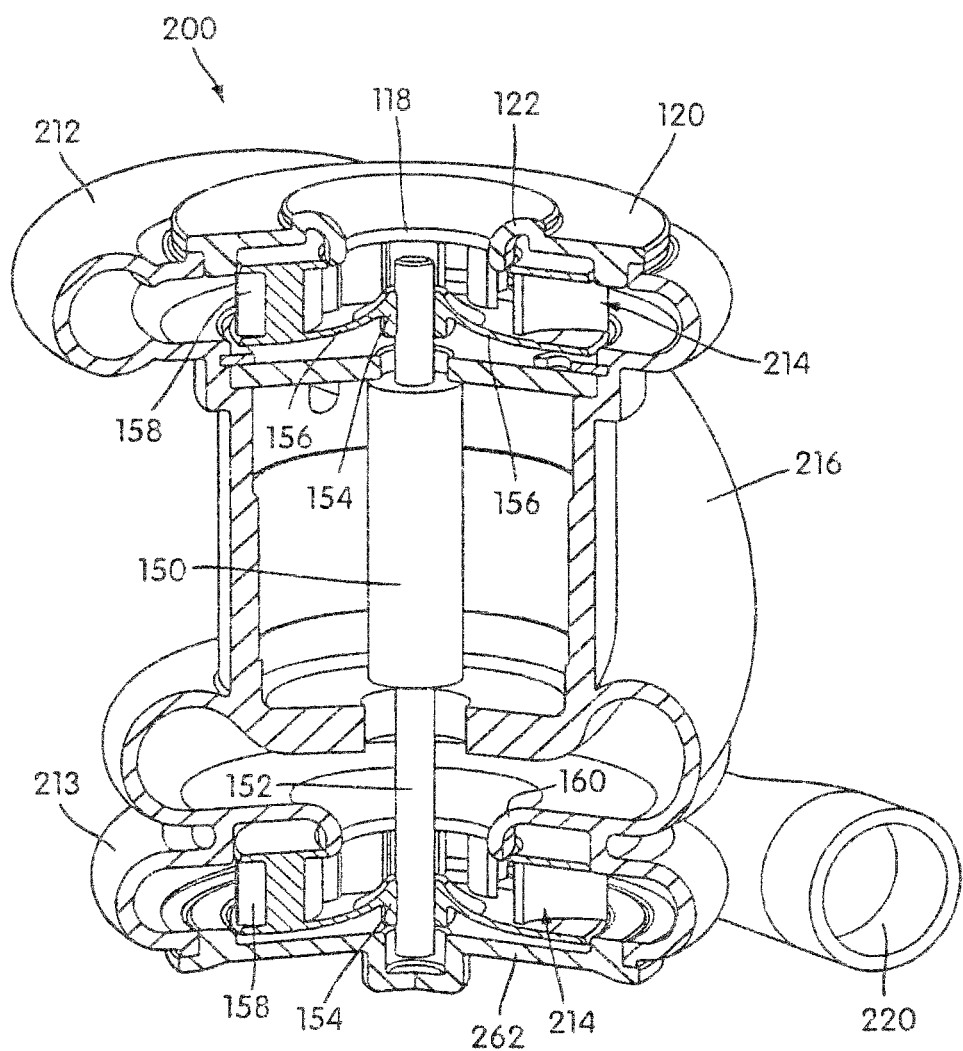
FIG. 5 is a sectional perspective view of the double-ended blower of FIG. 4.

FIGS. 4, 4A, and 5 illustrate a "same-handed" blower 200 according to the present invention. Blower 200 also has two volutes 212, 213, an airpath 216, an air intake 118 and an air outlet 220. However, as is shown in FIGS. 4, 4A, the airpath 216 has the shape of a spiral. That is, airpath 216 transitions away from the first volute 212 and then slopes downward as it follows the circumference of the blower 200, before bending and gradually fusing with an intake cavity located between the motor 150 and the arcuate flange 160 (See FIG. 5), which acts as an air intake in blower 200. The airflow through the blower 200 is illustrated by the arrows in FIGS. 4, 4A.

The internal configuration of blower 200 is shown in the partially sectional perspective view of FIG. 5. The internal arrangements of blowers 100 (FIGS. 1, 2) and 200 (FIGS. 4, 4A, 5) are substantially similar, and will be described below with respect to components of both blowers, where applicable. As shown in FIG. 5, a double-shafted electric motor 150 is installed in the center of the blower 200. Although only one motor 150 is shown, two motors 150, one for each impeller, may be used. Various types of known brackets and mountings may be used to support the motor and to secure it to the interior of the blower 200, although for simplicity, these are not shown in FIG. 5.

The motor 150 drives the double shaft 152 to rotate at speeds up to, e.g., about 30,000 RPM, depending on the configuration of the impellers 114, 115, 214 and the desired pressures. The shaft 152 traverses substantially the entire length of the blower 100, 200 along its center, and is secured to an impeller 114, 115, 214 at each end. The shaft may be round, square, keyed, or otherwise shaped to transmit power to the two impellers 114, 115, 214. The diameter of the shaft may be in the order of, e.g., 3-5 mm, with graduations in diameter along the length of the shaft 152. For example, the shaft 152 may have a smaller diameter (e.g., 3 mm) on the end closest to the air intake to assist with air intake and a diameter of about 4.5 mm at the end that is cantilevered. The connection between the impellers 114, 115, 214 and the shaft 152 may be created by an interference fit between the two parts, a weld, an adhesive, or fasteners, such as set screws. In blowers 100 and 200, the connection between the shaft 152 and the impellers 114, 115, 214 is by means of a vertically oriented (i.e., oriented along the axis of the shaft 152) annular flange 154 formed in the center of the impellers 114, 115, 214. In FIG. 5, the connection between the impeller 214 and the shaft is shown as an interference fit.

Figure 6A:
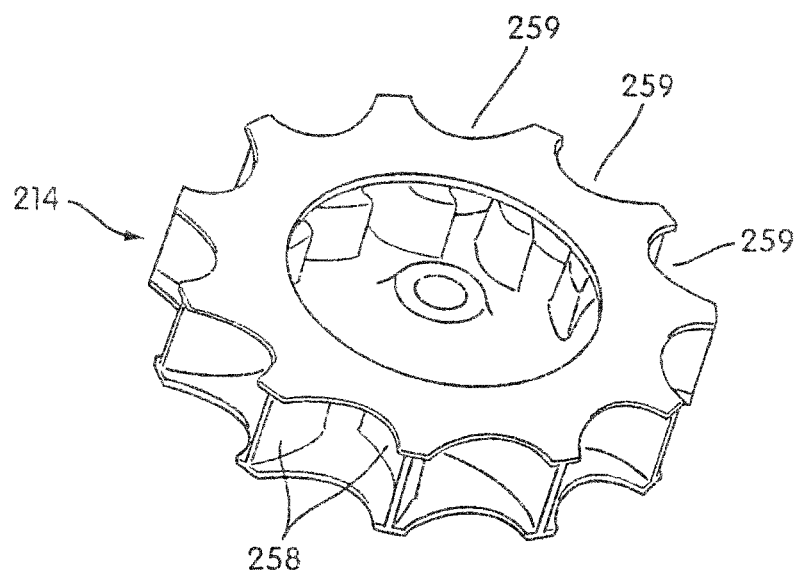
FIGS. 6A and 6B are a perspective view of an impeller having scalloped edges.
Figure 6B:
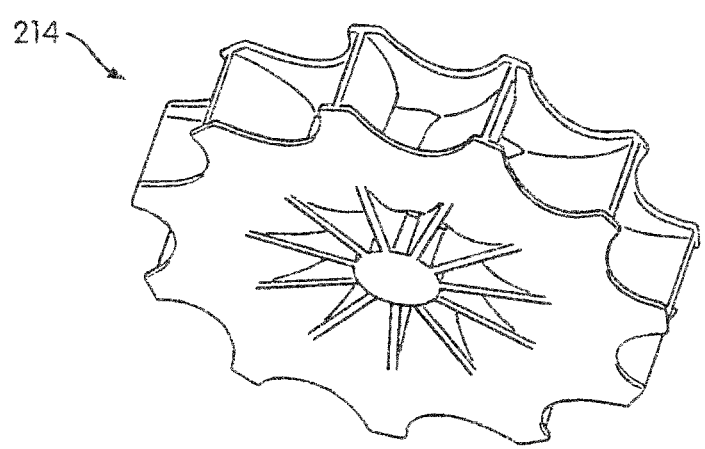

The impeller 114, 115, 214 is substantially annular in shape. The center section 156 of the impeller 114, 115, 214, is a thin plate which extends radially outward from the shaft 152 to the blades 158, and is upswept, gradually curving downward as it extends outward from the shaft 152 towards the blades 158. The actual diameter of each impeller 114, 115, 214 may be smaller than that of a conventional blower with a single impeller. Fast pressure rise time in a blower requires a low rotational inertia, which varies as the diameter to the fourth power. Because impellers 114 and 214 of blowers 100 and 200 are smaller in diameter, they have less rotational inertia, and thus, are able to provide a faster pressure rise time. In addition to diameter, other design parameters of the impellers 114, 214 may be modified to achieve a lower rotational inertia. Other techniques to reduce rotational inertia include "scalloping" the shrouds to produce a "starfish-shaped" impeller, using an internal rotor motor, and using materials, such as liquid crystal polymer, that can be molded into thinner wall sections, so that impeller blades can be hollowed out and strengthened by ribs. The scalloping of the impellers may also advantageously result in a weight reduction of the impeller, therewith allowing faster rise times. See also FIGS. 6A and 6B (starfish shaped impeller 214 with aerofoil blades 258 and scalloped edges 259). Liquid crystal polymer impeller blades may have wall sections as low as 0.3 mm.

In embodiments of the invention, the impellers 114, 115, 214 would typically have an outer diameter in the order of, e.g., 40-50 mm, for example 42.5 mm or 45 mm. The inner diameter of the impellers 114, 115, 214 may be in the order of, e.g., 18-25 mm. Blade height may be in the range of, e.g., 6-10 mm, although stresses on the impeller blades 158 increases with taller blades. In general, if the blades 158 are taller, the diameter of the impeller may be reduced. The impeller blades 158 themselves may be aerofoils of standard dimensions, such as the NACA 6512, the NASA 66-221, and the NASA 66-010. If the blades 158 are aerofoils, it may be advantageous to select aerofoil profiles that produce good lift at a variety of angles of attack. The impellers 114, 115, 214 are preferably designed and/or selected so that, in cooperation with the motor, the blower 100, 200 can generate a pressure at the mask of about 25 cm $H_2O$ at 180 L/min and about 30 cm $H_2O$ at 150 L/min. Given that the airpath 116 will cause pressure drops from the blower 100, 200 to the mask, the impellers 114, 115, 214 are preferably capable of producing about 46 cm $H_2O$ at 150 L/min and about 43 cm $H_2O$ at 180 L/min.

The top of the first volute 112, 212 is open, forming the air intake 118. At the air intake 118, the top surface 120 of the blower 100, 200 curves arcuately inward, forming a lip 122 over the top of the impeller 114, 214. The upswept shape of the impeller center section 156 and the lip 122 of the top surface 120 confine the incoming air to the blower volume inside the first volute 112, 212 and help to prevent air leakage during operation. An arcuate flange 160 similar to the arcuate top surface 120 extends from the lower interior surface of the blower 200, forming the top of the second volute 213. A contoured bottom plate 162, 262 forms the bottom of the second volute 113, 213 of each blower 100, 200. The bottom plate 162 of blower 100 has a hole in its center, allowing the airpath 116 to enter, while the bottom plate 262 of blower 200 has no such hole. As described above, the arcuate flange 160 acts as the air intake for the second volute 213 of blower 200. In blower 200, stator vanes and additional flow shaping components may be added to the cavity between the motor 150 and the arcuate flange 160 to assist in distributing the incoming air so that it enters the second volute 213 from all sides, rather than preferentially from one side.

As is evident from FIGS. 1, 2, 4A, and 5, blowers according to the present invention may have many intricate and contoured surfaces. Such contours are used, as in the case of the arcuate top surface 120 and arcuate flange 160, to direct gas flow and prevent gas leakage. The no-leak feature is particularly beneficial when the gas flowing through the blower 100, 200 has a high concentration of oxygen gas. If high-concentration oxygen is used, gas leakage may pose a safety hazard. Also, apart from any safety considerations, leaking gas may produce unwanted noise, and may reduce blower performance.

The number of intricate, contoured surfaces present in blowers in embodiments according to the present invention makes a production method such as investment casting particularly suitable. Investment casting can produce a single part with many hidden and re-entrant features, whereas other methods of production may require that a design be split into many parts to achieve equivalent function. However, a large number of parts is generally undesirable—in order to minimize the potential for gas leaks, the number of parts is best kept to a minimum and the number of joints between parts is also best kept to a minimum.

There are also a number of materials considerations for blowers according to the present invention. Metals are typically used in investment casting, but some metals are particularly sensitive to oxidation, which is a concern because medical grade oxygen gas may be used in blowers according to the present invention. One particularly suitable material for the blowers 100, 200 is aluminum. Whereas steel may rust on exposure to high concentrations of oxygen, aluminum oxidizes quickly, the oxide forming an impervious seal over the metal. Whichever metal or other material is used, it is generally advantageous that the material has a high thermal conductivity and is able to draw heat away from the airpath, to prevent any heat-related ignition of oxygen.

While the use of aluminum has many advantages, it does have a tendency to "ring," or resonate, during blower operation. Therefore, damping materials may be installed in an aluminum blower to reduce the intensity of the vibration of the aluminum components.

In blowers 100 and 200, the electric motor 150 may be driven at variable speeds to achieve the desired IPAP and EPAP pressures. The double-ended (i.e., two-stage) design of the blowers means that the range of motor speeds traversed to achieve the two pressures is reduced. The narrower range of motor speeds results in a faster pressure response time than that provided by a single-stage blower having similar motor power and drive characteristics. In addition, the narrower variation in speed applies less stress to the rotating system components, resulting in increased reliability with less acoustic noise.

The performance of blowers 100 and 200 is approximately equal to the combined performance of the two impeller/volute combinations, minus the pressure/flow curve of the airpath 116, 216 between the two volutes 112, 113, 212, 213. For a variety of reasons that are well known in the art, the actual performance of the blowers 100, 200 will depend upon the instantaneous flow rate of the particular blower 100, 200, as well as a number of factors. At higher flow rates, the pressure drop in the airpath 116, 216 is generally more significant.

Double-ended blowers according to the present invention may be placed in a CPAP apparatus in the same manner as a conventional blower. The blower is typically mounted on springs, or another shock-absorbing structure, to reduce vibrations.

A Further Embodiment

Figure 7:
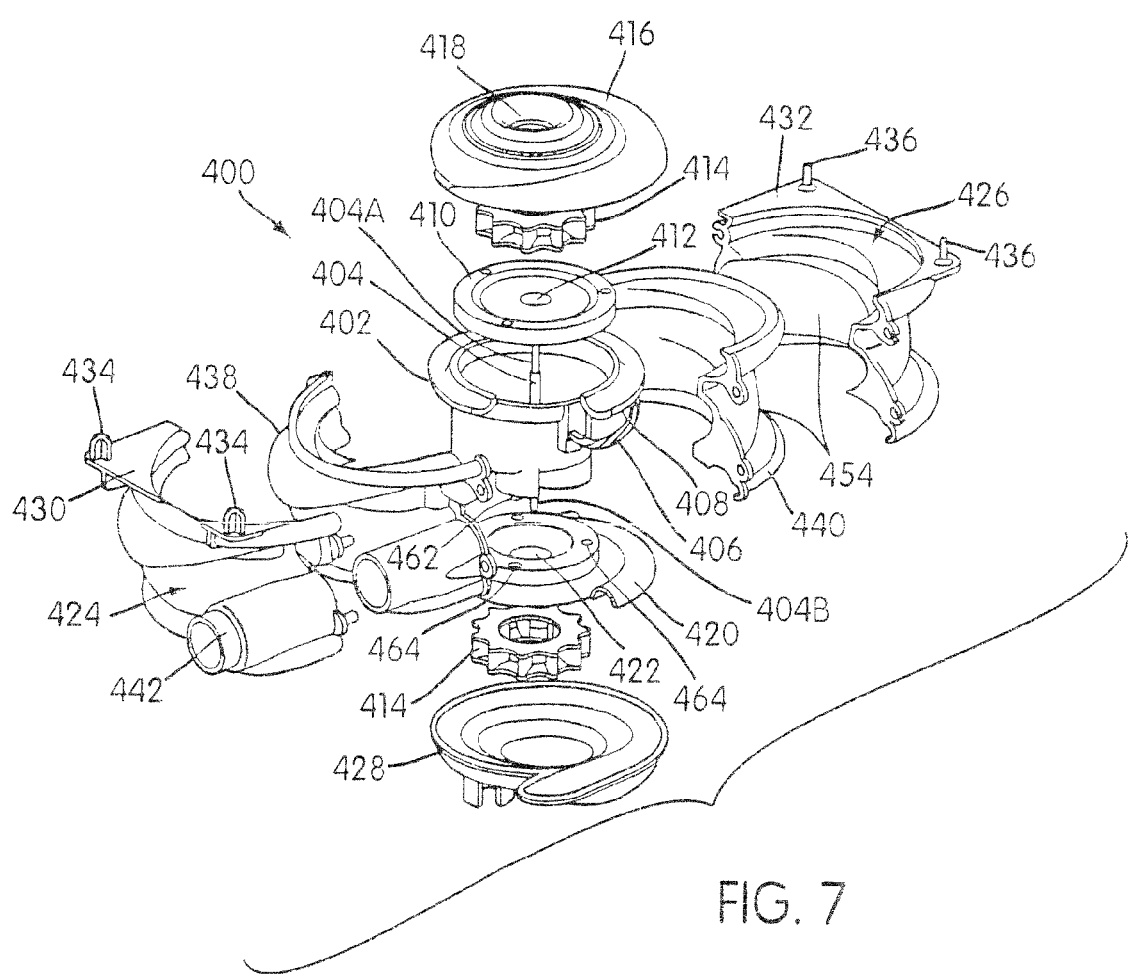
FIG. 7 is an exploded perspective view of a double-ended blower according to another embodiment of the present invention.

A further embodiment of the present invention is illustrated in FIG. 7, an exploded perspective view of a double-ended blower 400 according to the present invention. The motor and stator blade portion 402, located in the center of the exploded view, is investment cast from aluminum in this embodiment, although other manufacturing methods are possible and will be described below. The aluminum, as a good conductor of heat, facilitates the dissipation of heat generated by the accelerating and decelerating motor. Each end 404A and 404B of the shaft 404 is shown in FIG. 7, but the motor windings, bearing and cover are not shown. The motor power cord 406 protrudes from the motor and stator blade portion 402. The motor and stator blade portion 402 includes, at its top, a bottom portion of the upper volute 408.

As a variation of the design illustrated in FIG. 7, the motor and stator blade portion 402 may be made separately from the bottom portion of the upper volute 408. If the two components are made separately, investment casting would not be required. For example, the motor body may be die cast, while the bottom portion of the upper volute 408 may be injection molded.

Figure 7B:
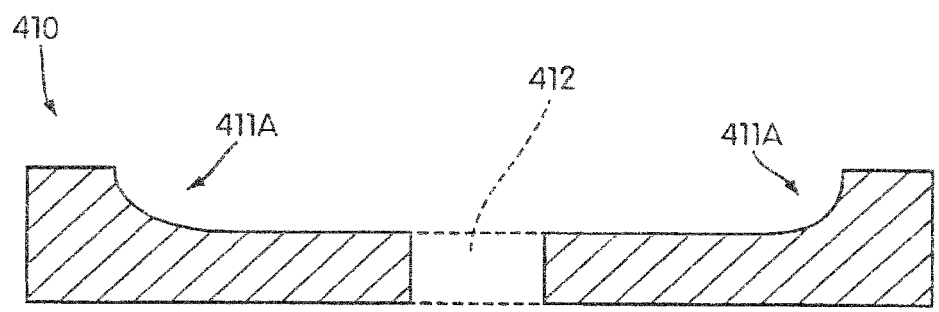
FIG. 7B is a cross-sectional view of an alternative embodiment of the circular plate in FIG. 7A.

Secured to the motor and stator blade portion 402 by bolts or other fasteners is a circular plate 410, in which a hole 412 is provided for the passage of the shaft 404. An impeller 414 rests atop the circular plate. The impeller 414 is scalloped along its circumference to reduce its rotational inertia, giving it a "starfish" look (see also FIGS. 6A and 6B). As depicted in more detail in FIG. 7A, the contoured plate has a side 411 that extends perpendicular to the annular surface 413. In another embodiment, schematically shown in FIG. 7B, the side 411A extends more gradually from the annular surface. Having side 411A extend more gradually facilitates, relative to the perpendicular side 411, the air flow created by impeller 414 and therewith aids in noise suppression. Hole 412 is depicted in FIG. 7B as being of constant radius. In one embodiment, hole 412 may neck down or have a diameter of non-constant cross-section.

Referring back to FIG. 7, an upper endcap 416 is secured above the impeller 414, and provides the top portion of the upper volute. The upper and lower volutes in this embodiment are versions of the in-plane transitional scroll volute 300 illustrated in FIG. 3. An aperture 418 in the center of the upper endcap 416 serves as the air intake of the blower 400.

On the lower end of the blower 400, a contoured plate 420 forms the top portion of the lower volute. As depicted in more detail in FIG. 7A, the motor and stator blade portion 402 may comprise feet 462 that can be connected to contoured plate 420 via press-fit recesses 464. The motor 402 and contoured plate may also be connected instead or in addition via, e.g., adhesives, screws etc. or, alternatively, the motor 402 and contoured plate 420 may be cast as a single piece.

The top of the contoured plate 420 is raised and curves arcuately downward toward a hole 422. As was explained above, the contoured plate 420 helps to shape the airflow and to ensure that it enters the impeller cavity from all sides, rather than preferentially from a single direction. Beneath the contoured plate 420, a lower impeller 414 rotates proximate to a lower endcap 428. The two endcaps, 416, 428 may be die cast (e.g., from aluminum or magnesium alloy) or they may be injection molded from an appropriate metal.

The outer sidewalls of the airpaths in the upper and lower volutes are essentially defined by the damping sleeves 438 and 440. The damping sleeves are inserted into left side casing 424 and right side casing 426. The left side casing 424 provides the air outlet 442 for the blower 400. The left 424 and right 426 side casings are secured together with, e.g., bolts or other removable fasteners. On the top surface of the side casings 424, 426 are square flanges 430, 432 having protrusions 434, 436 that allow the blower 400 to be mounted on springs inside a CPAP apparatus. In FIG. 7, the protrusions 434, 436 are shown as having different sizes and shapes, however, in FIGS. 8 and 9, the protrusions 434 are shown as having the same shape. It will be realized that the protrusions 434, 436 may take either of the depicted shapes, or any other shape, depending on the properties and arrangement of the springs onto which the blower 400 is mounted.

In one embodiment, the damping sleeves 438, 440 are rubber or foam rubber components that are, e.g., injection molded to match the internal contours of the left 424 and right 426 side casings, respectively. In one implementation, the damping sleeves 438, 440 are 40 Shore A hardness polyurethane formed from a rapid prototype silicone mold.

Alternatively, the damping sleeves 438, 440 could be silicone, or another elastomer that is stable at the high temperatures generated by the motor. The damping sleeves 438, 440 serve three major purposes in blower 400: (i) they define (part of) the airpaths in the upper and lower volutes, (ii) they provide a seal between the other components, and (iii) they dampen the vibrations of the other parts.

Figure 8:
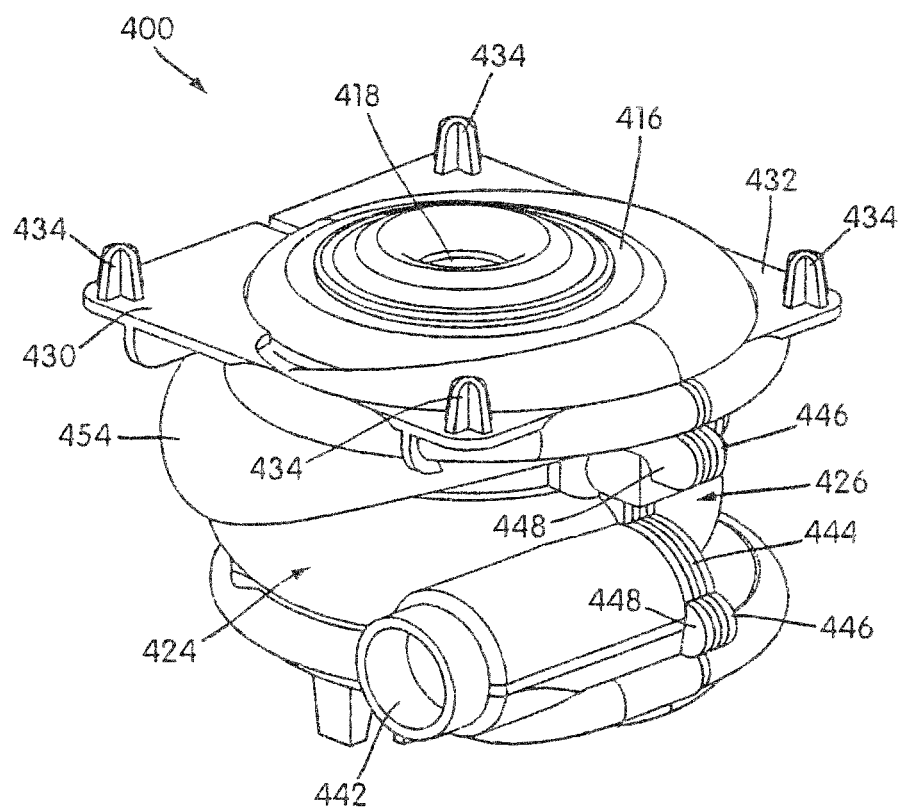
FIG. 8 is an assembled perspective view of the double-ended blower of FIG. 7 from one side.
Figure 9:
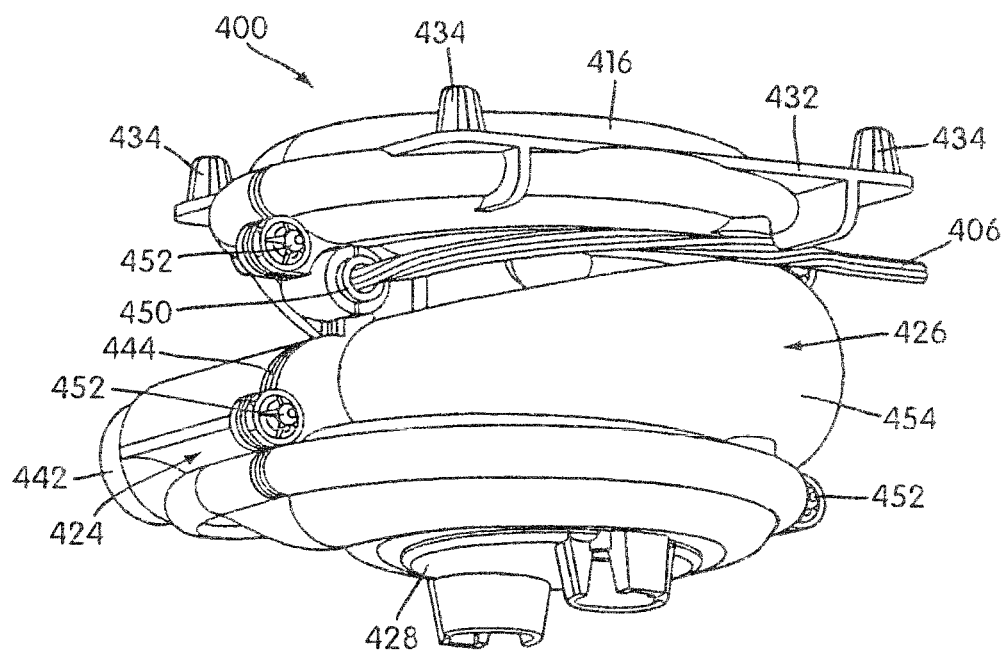
FIG. 9 is an assembled perspective view of the double-ended blower of FIG. 7 from another side.

FIG. 8 is an assembled perspective view of blower 400 from one side. The assembled air outlet 442 is shown in FIG. 8, as is the seam 444 between the left 424 and right 426 side casings. As shown in FIG. 8, flanges 446, 448 protrude laterally from the edge of each side casing 424, 426 and abut to form the seam 444. As shown in FIG. 9, the two side casings 424, 426 are secured together by bolts 452 that pass through the flange 446 provided in the right side casing 426 and into threaded holes provided in the flange 448 of the left side casing 424. Furthermore, the power cord 406 exits the assembled blower through a sealed orifice 450 (see FIG. 9)

Blower 400 has several advantages. First, investment casting is not required to produce blower 400, which reduces the cost of the blower. Additionally, because the components of blower 400 have fewer hidden and intricate parts, the castings can be inspected and cleaned easily. Finally, blower 400 is easier to assemble than the other embodiments because the components are clamped together using the two side casings 424, 426, which can be done with simple fasteners.

Another Embodiment

Figure 10:
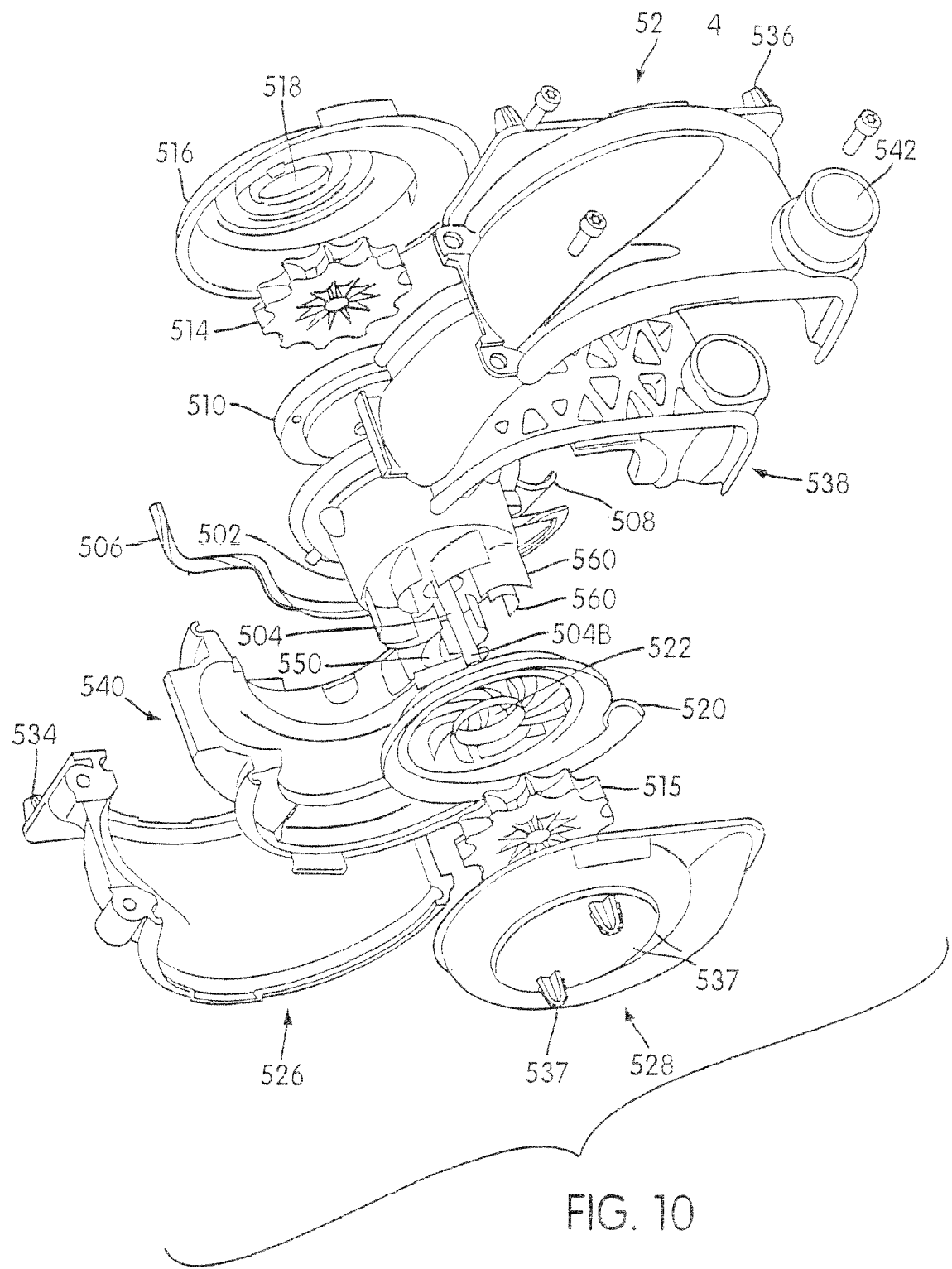
FIG. 10 is an exploded perspective view of a double-ended blower according to a further embodiment of the present invention.

Another embodiment of the present invention is illustrated in FIG. 10, an exploded perspective view of a double-ended blower 500 according to the present invention. The motor 502, located in the center of the exploded view, is investment cast from aluminum in this embodiment, although other manufacturing methods are possible and will be described below. The aluminum, as a good conductor of heat, facilitates the dissipation of heat generated by the accelerating and decelerating motor. Examples of suitable motors are described, for instance, in U.S. provisional application 60/452,756, filed Mar. 7, 2003, which is hereby incorporated in its entirety by reference. The shaft 504 has two ends (only one end 504B is shown in FIG. 10, but compare end 404A in FIG. 7) to which the impellers 514, 515 can be functionally connected. The motor power cord 506 protrudes from the motor 502 and exits the blower 500 through recess 550 (see also FIG. 11A) in damping sleeve 540. Damping sleeve 538 comprises a substantially corresponding protrusion 552 (See FIG. 11B) to minimize or avoid airflow leaks and to reduce the risk of pulling forces on the power cord being transferred to the power cord/motor connection. In one embodiment, shown in FIGS. 11A and 11B, protrusion 552 comprises ribs 554 that substantially interlock with ribs 556 in recess 550 to further minimize airflow leaks. Also, in one embodiment the wires in the motor power cord are silicon rubber covered wires (allowing increased flexibility and noise suppression).

Figure 12:
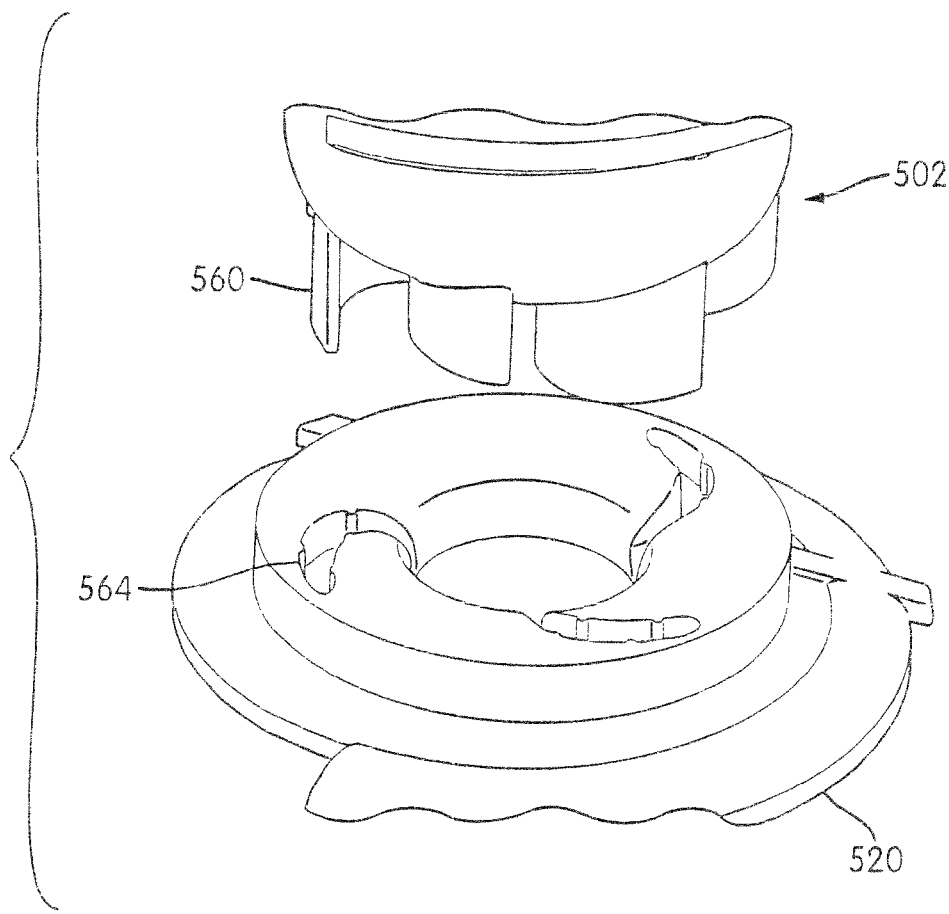
FIG. 12 is a perspective view of the press-fit connection between stationary flow guidance vanes and the contoured plate in FIG. 10.

The motor 502 comprises stationary flow guidance vanes 560, which may be aerofoil shaped. The vanes 560 are capable of changing the direction of the airflow arriving at the vanes 560 through the spiral airpath defined by damping sleeves 538, 540 from tangential to radial, i.e. towards the hole 522. As depicted in more detail in FIG. 12, the motor 502 can be connected to contoured plate 520 via press-fit recesses 564 in contoured plate 520 for some of the vanes 560. Other ways to connect motor 502 to contoured plate 520 may also be used (e.g. screws or adhesives).

In one embodiment, the motor 502 includes, at its top, a portion 508 of the upper volute. As a variation of the design illustrated in FIG. 10, the motor 502 may be made separately from the portion 508 of the upper volute. If the two components are made separately, the motor body may, for instance, be die cast, while the portion 508 of the upper volute may be, for instance, injection molded.

Secured to the motor 502 by bolts or other fasteners is a circular plate 510, in which a hole is provided (not shown, but compare hole 412 in FIG. 7) for the passage of the shaft 504.

The impellers 514, 515, connected to the ends of the shaft 504, are scalloped along their circumference to reduce rotational inertia, giving them a "starfish" look.

An upper endcap 516 is secured above impeller 514, and provides the top portion of the upper volute. An aperture 518 in the center of the upper endcap 516 serves as the air intake of the blower 500.

On the lower end of the blower 500 in FIG. 10, a contoured plate 520 forms the top portion of the lower volute. The bottom of the contoured plate 520 is curved arcuately upward toward a hole 522. Part of the bottom of contoured plate 520 is ribbed. Beneath the contoured plate 520, an impeller 515 rotates proximate to a lower endcap 528, which comprises two protrusions 537. The two endcaps, 516, 528 may be die cast (e.g., from aluminum or magnesium alloy) or they may be injection molded from an appropriate metal.

The side casing 524 defines air outlet 542 for the blower 500. The side casings 524 and 526 are secured together with bolts or other removable fasteners. On the top surface of the side casings 524, 526 are protrusions 534, 536 that allow the blower 500 to be mounted on springs inside a CPAP apparatus. It will be realized that the protrusions 534, 536 may take any shape depending on the properties and arrangement of the springs onto which the blower 500 is mounted.

The double-ended blower 500 includes two damping sleeves 538, 540. The damping sleeves 538, 540 are, e.g., rubber or foam rubber components that are, e.g., injection molded to match the internal contours of the side casings 524, 526, respectively. In one implementation, the damping sleeves 538, 540 are formed from a rapid prototype silicone mold. Alternatively, the damping sleeves 538, 540 may be, for instance, silicone or another elastomer that is stable at the temperatures generated by the motor.

Figure 11A:
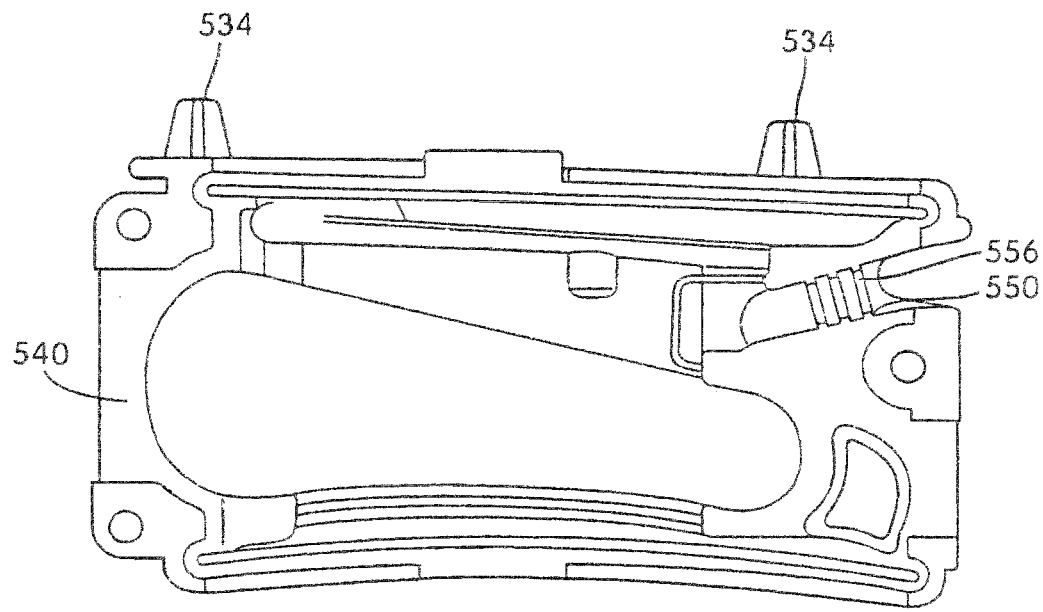
FIG. 11A is a side view of a first damping sleeve fitted into a casing of the blower represented in FIG. 10.
Figure 11B:
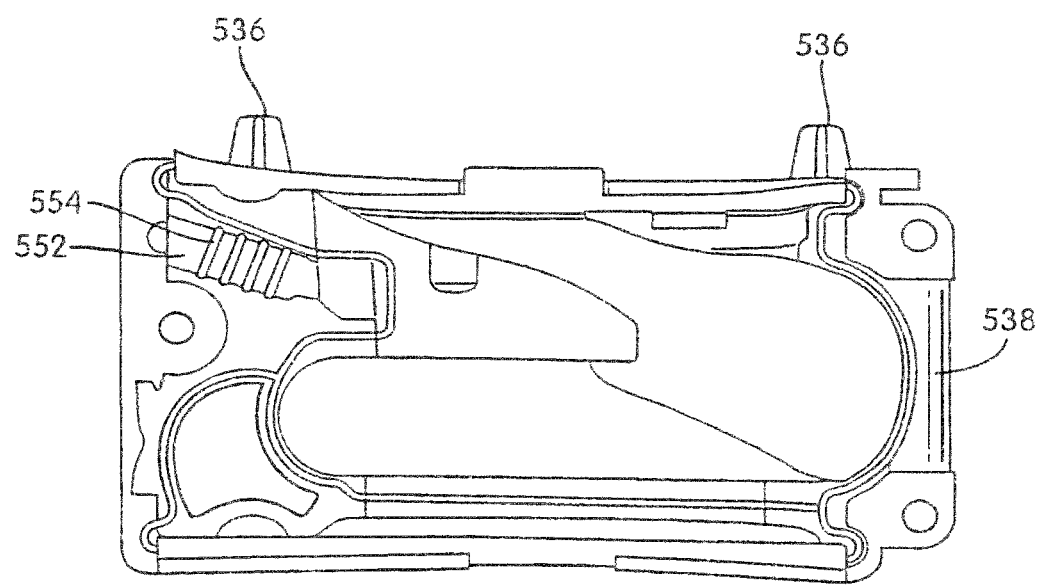
FIG. 11B is a side view of a second damping sleeve fitted into a casing of the blower represented in FIG. 10.

As is evident from FIGS. 10, 11A and 11B. the combination of damping sleeves 538, 540 defines, along with the components (e.g. motor 502) positioned between the sleeves, a spiral airpath/conduit. The portion of the spiral conduit defined by damping sleeve 540 has a decreasing cross-sectional area in the direction of airflow.

Figure 13:
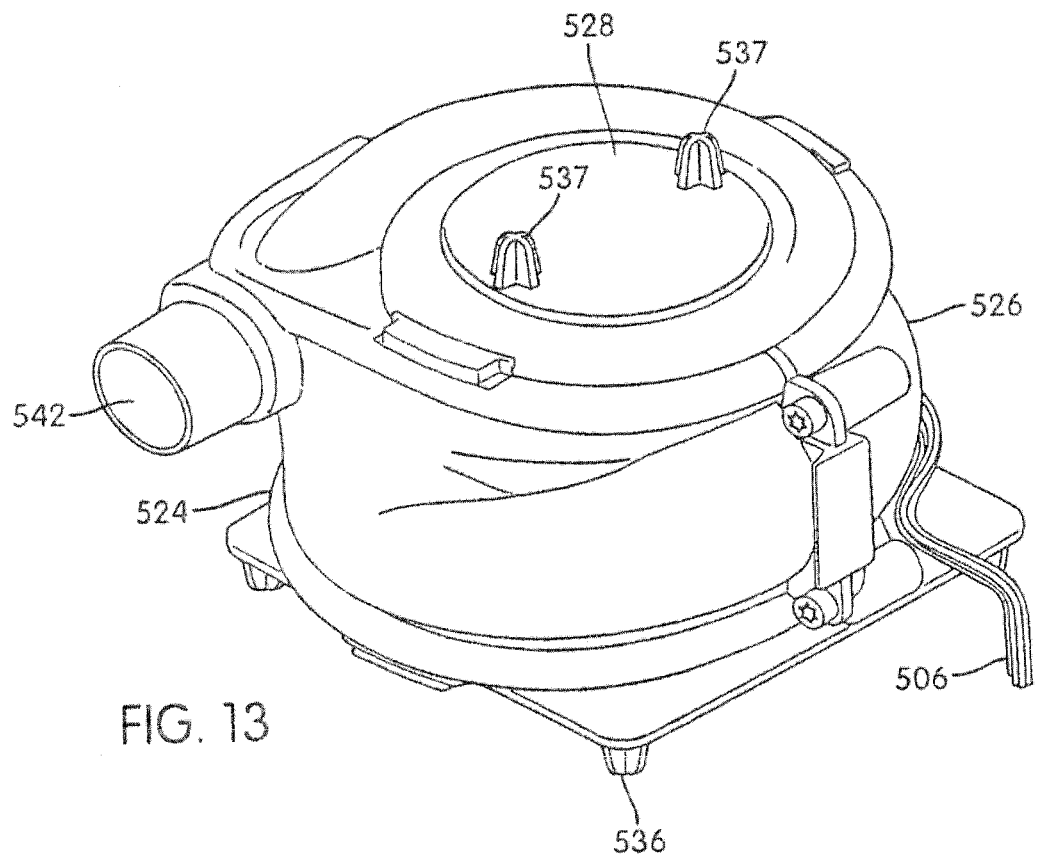
FIG. 13 represents an assembled view of the blower of FIG. 10.

FIG. 13 is an assembled perspective view of blower 500 (180° rotated with respect to FIG. 10).

In operation, blower 500 takes in air at aperture (external inlet) 518 through rotation of impeller 514. The air is transported through the spiral conduit defined by damping sleeves 538, 540 to the stationary flow guidance vanes 560, which substantially change the velocity vector of the arriving air from primarily tangential to primarily radial, i.e. toward internal inlet 522. Rotation of impeller 515 then transports the air arriving through hole (internal inlet) 522 via a second airpath (defined primarily by the space between lower endcap 528 and contoured plate 520) to external air outlet 542.

Figure 13A:
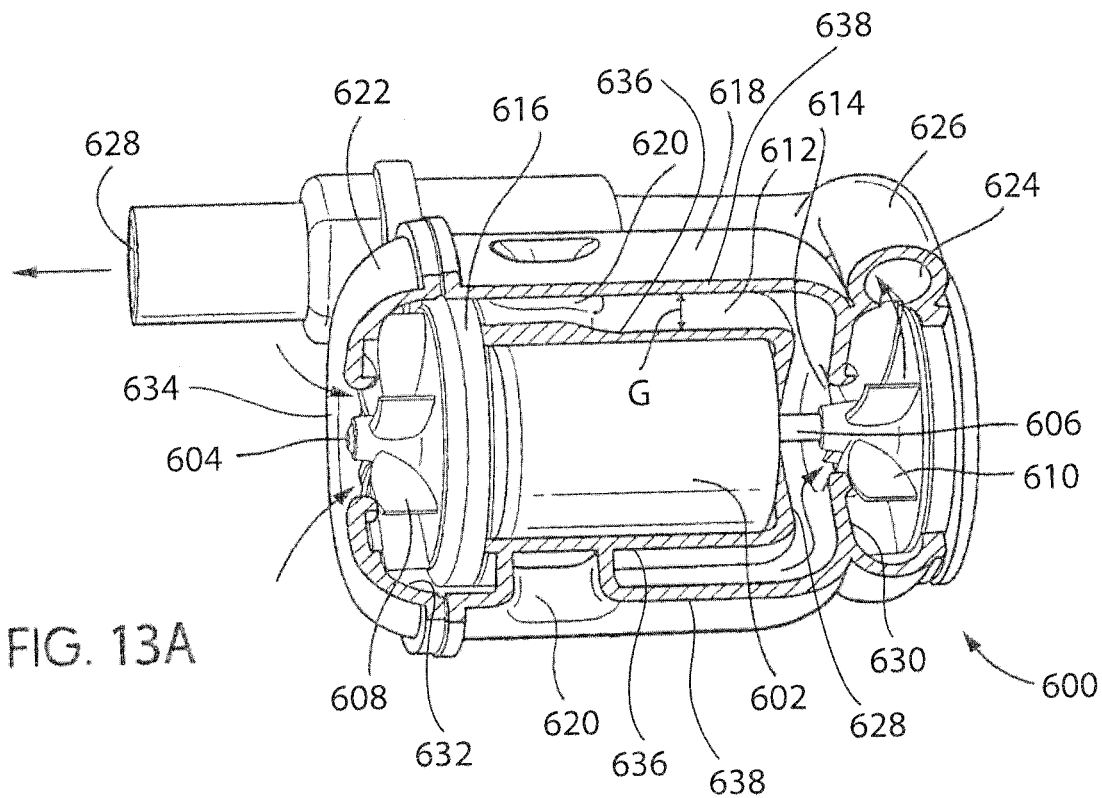
FIG. 13A is a partial cross-sectional view of a blower according to another aspect of the technology.
Figure 14:
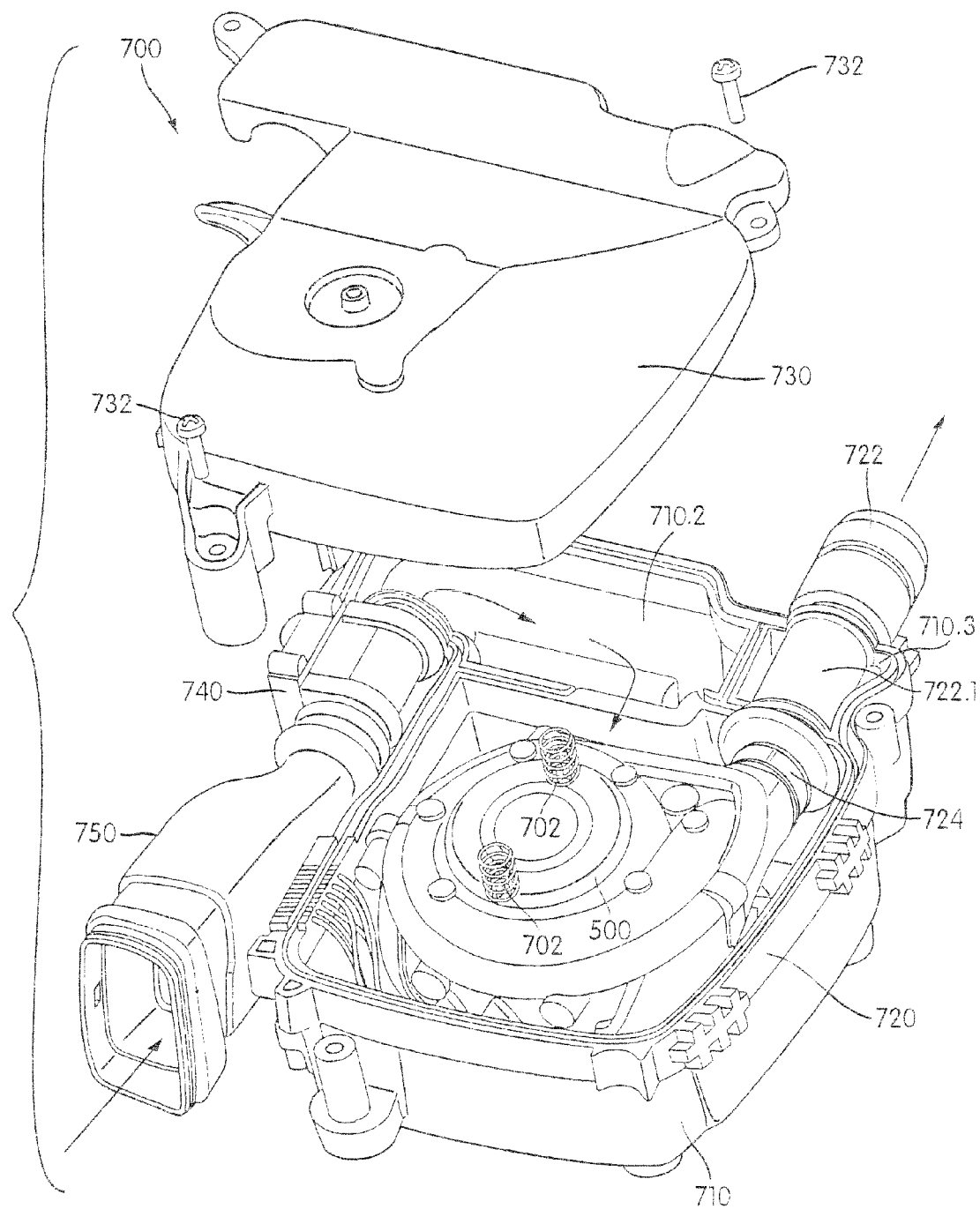
FIG. 14 is an exploded perspective view of an enclosure for a blower according to the present invention.
Figure 15:
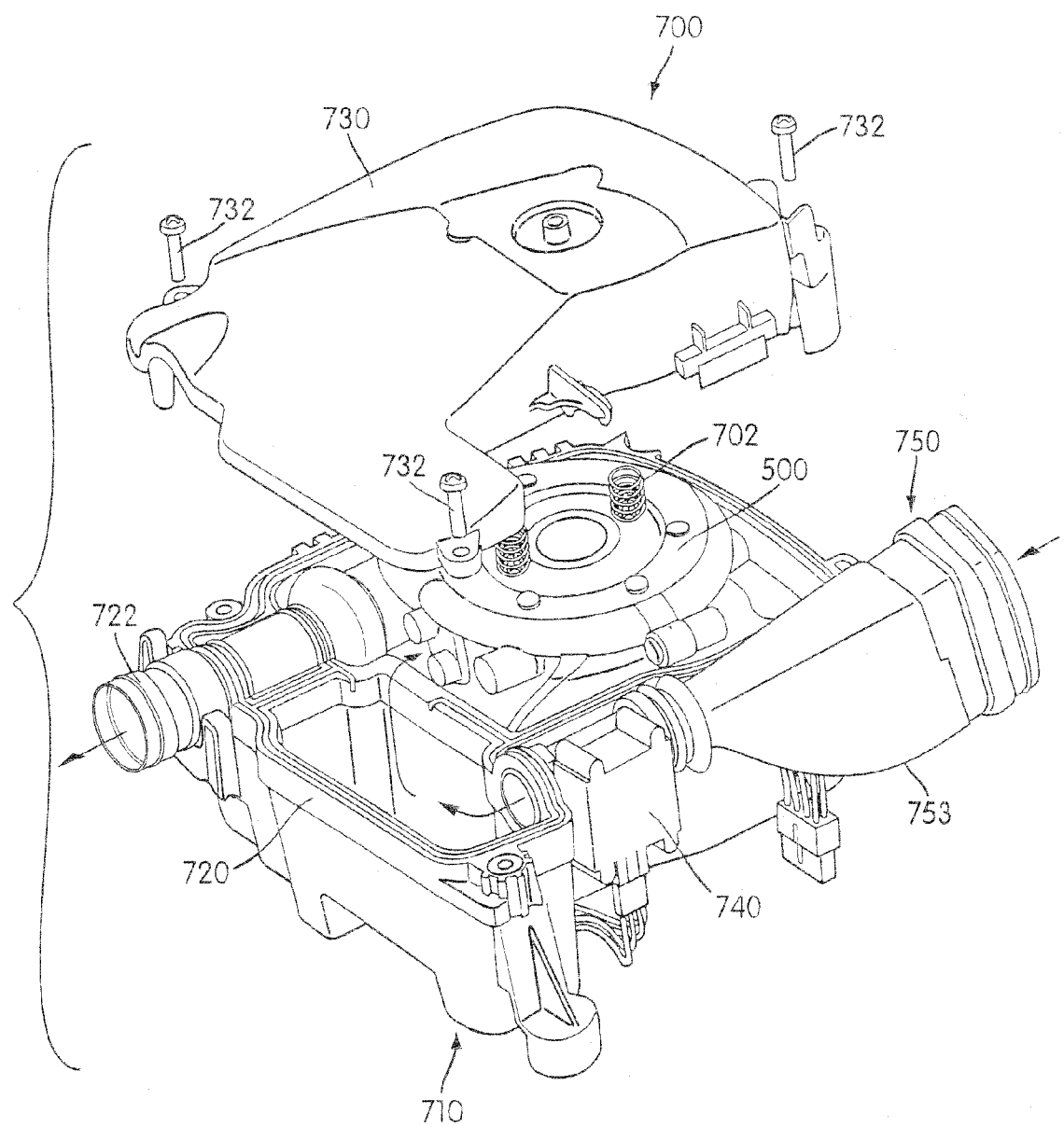
FIG. 15 is a further exploded perspective view of an enclosure for a blower according to the present invention.
Figure 16:
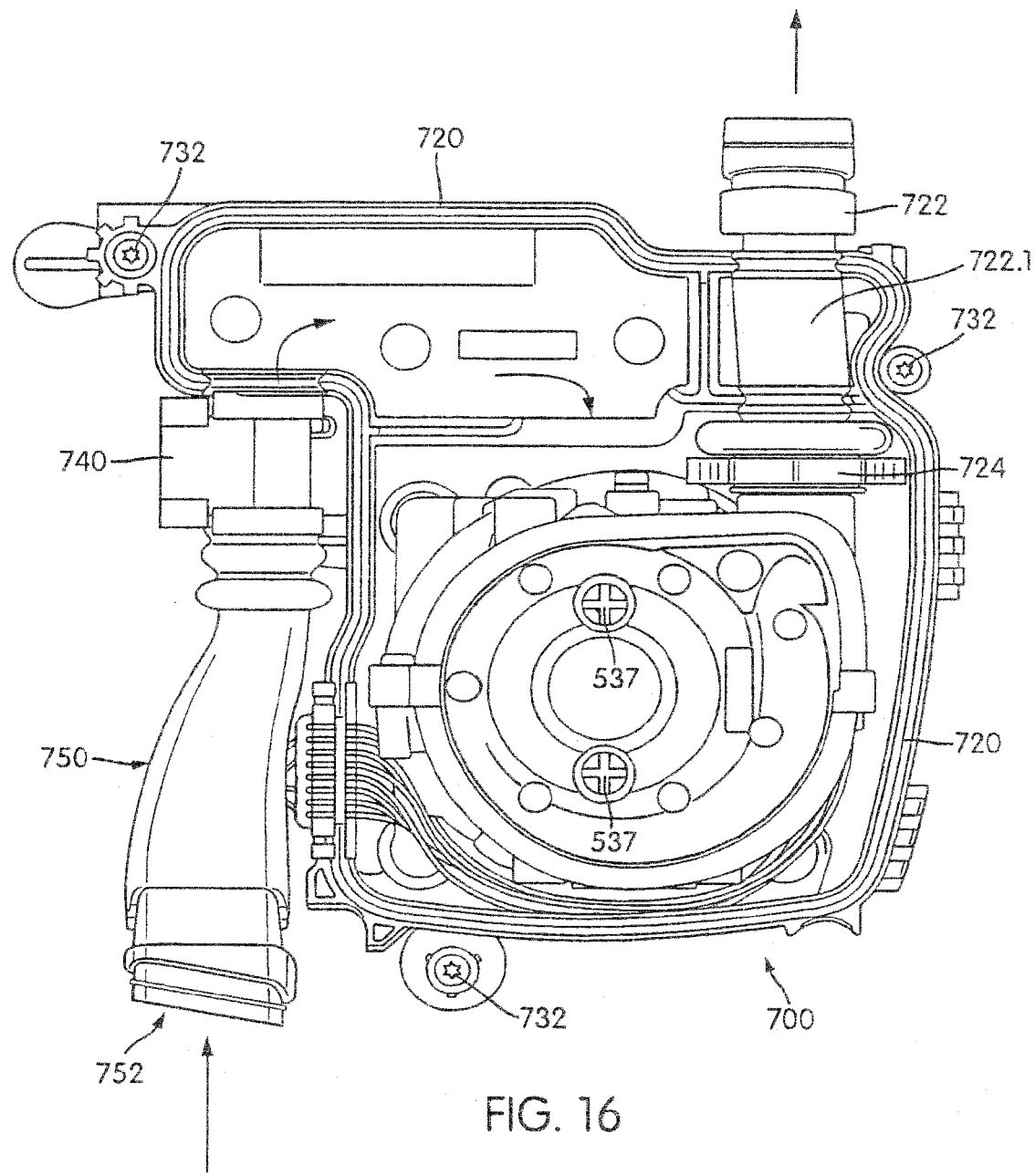
FIG. 16 is a top perspective view of the enclosure of FIG. 14.
Figure 17:
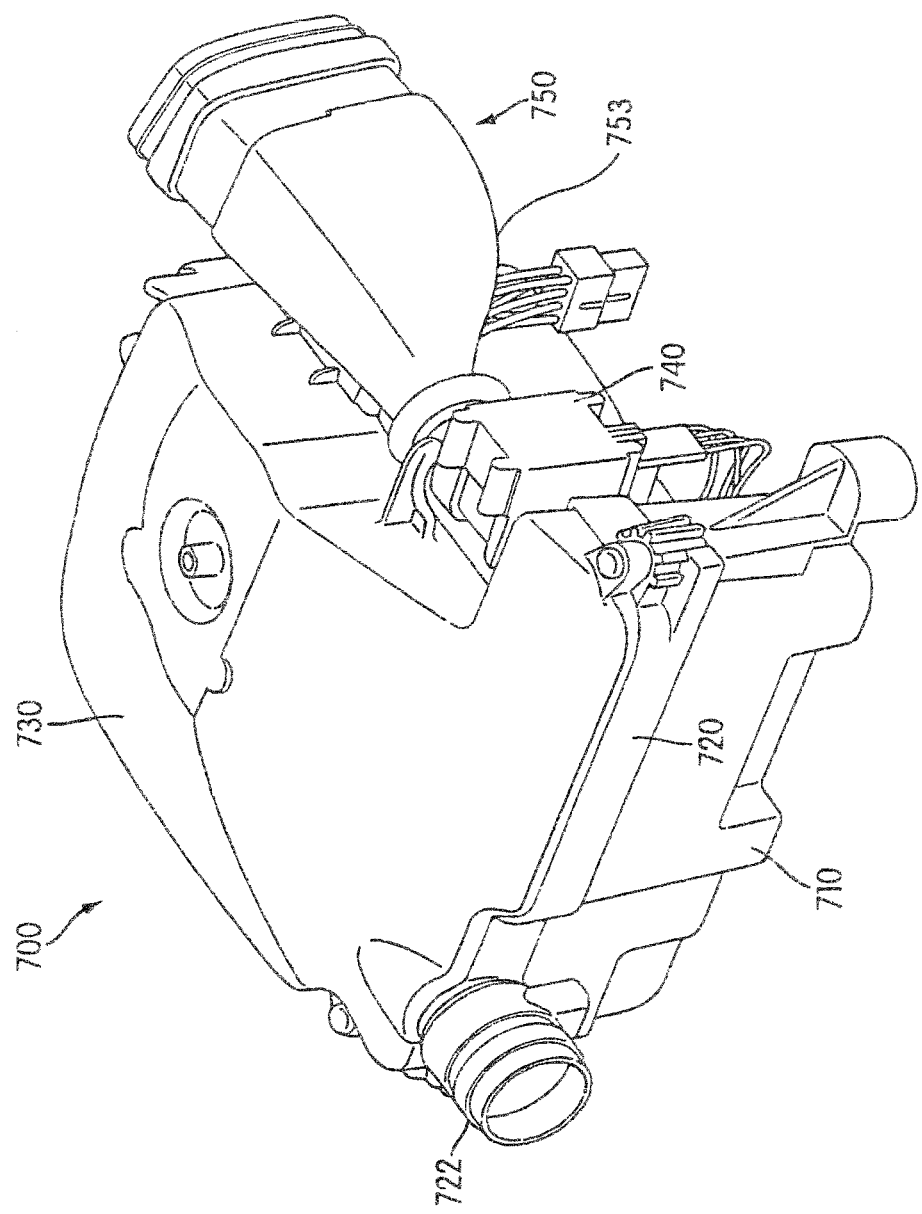
FIG. 17 represents an assembled view of the enclosure of FIG. 14.

FIG. 13A illustrates a partial cross-sectional view of a blower 600 according to another embodiment of the present invention. Blower 600 includes a motor 602 having a pair of opposed shafts 604 and 606 that connect to respective first and second stage impellers 608 and 610, respectively. Motor 602 is supported by an inner casing 612 that includes an aperture 614 leading to the second stage impeller 610 to allow for passage of shaft 606. A lid 616 is provided to the first stage end of casing 612, and includes an aperture to accommodate passage of shaft 604.

An outer casing 618 is provided to support inner casing 612 via one or more support members 620, two of which are shown in FIG. 13A. The inner and outer casings 612, 618 are spaced from one another by a gap G, which defines a channel adapted for the passage of pressurized gas from the first stage to the second stage. The gap G is defined by a generally annular chamber between adjacent side walls 636, 638 of the inner and outer casings. The channel is also formed between bottom walls 628, 630 of the inner and outer casings.

In operation, gas, e.g., air, is directed through blower 600 as indicated by the arrows. In particular, gas is drawn in towards the first stage impeller 608 through an aperture 634 provided in cap 622. First stage impeller 608 forces the air radially outwards, such that the air follows a path along the inside domed surface 632 of the cap 622. Air then proceeds along the gap G provided between inner and outer casings 612, 618, passing along support members 620. Air moves radially inwardly between bottom walls 628, 620 and then proceeds through aperture 614 towards second stage impeller 610. Second stage impeller forces the air radially outwards and into an inlet 624 of conduit 626, whereby the now pressurized gas is directed to outlet 628, for delivery to a patient interface (e.g., mask) via an air delivery conduit (not shown).

Figure 18:
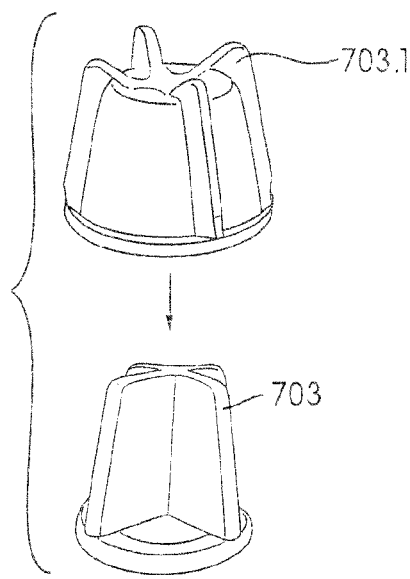
FIG. 18 is a perspective view of a protrusion of a blower according to the present invention provided with a rubber suspension bush.

FIGS. 14-17 show an embodiment wherein blower 500 is placed in an enclosure 700. The blower 500 is mounted in the enclosure on springs 702 that are provided over all six protrusions 534, 536, and 537 (only the springs provided over protrusions 537 are shown). The springs aid in reducing vibration and noise. In another embodiment, suspension bushes (e.g. rubber suspension bushes) are provided over the protrusions instead of springs 702 to reduce vibration and noise. An example of a rubber suspension bush 703.1 provided over a protrusion 703 is shown in FIG. 18.

The enclosure 700 comprises a main seal 720. See also FIG. 19. Outlet 722 of main seal 720 is connected to outlet 542 of blower 500 and securely fastened with a spring clip 724 (outlet 542 is shown in FIG. 10). Main seal 720 is positioned between enclosure base 710 and enclosure lid 730, which are connected using screws 732. In one embodiment, the enclosure base 710 and the enclosure lid 730 are made of metal, e.g. aluminum. For example, the enclosure base 710 and enclosure lid 730 are made form die cast aluminum. One of the advantages of aluminum is its good corrosion/burn resistance, even in oxygen rich environments. The aluminum has sufficient mass to resist movement and therefore serves to attenuate noise generated by the working of the blower. However if the aluminum resonates and thereby generates a ringing noise, that ringing noise can be attenuated/eliminated by the use of the main seal 720, e.g., a silicone gasket. Seal 720 also works well with the enclosure's aluminum casing sections to achieve the desired leak free seal. In this embodiment only three holding points (which use screws) are required to apply the force necessary to achieve the leak free joining of the seal between the two aluminum-casing sections.

Figure 19A:
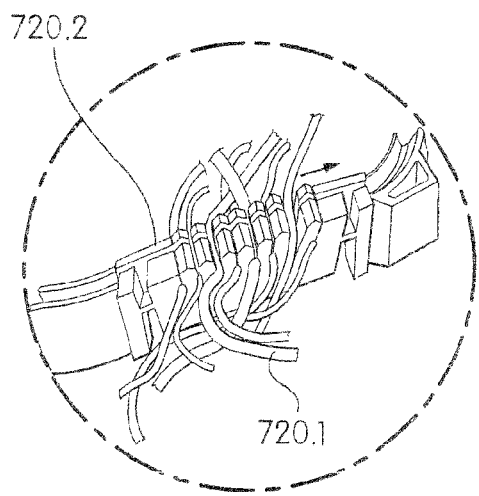
FIG. 19A is a detailed view taken from FIG. 19.
Figure 19:
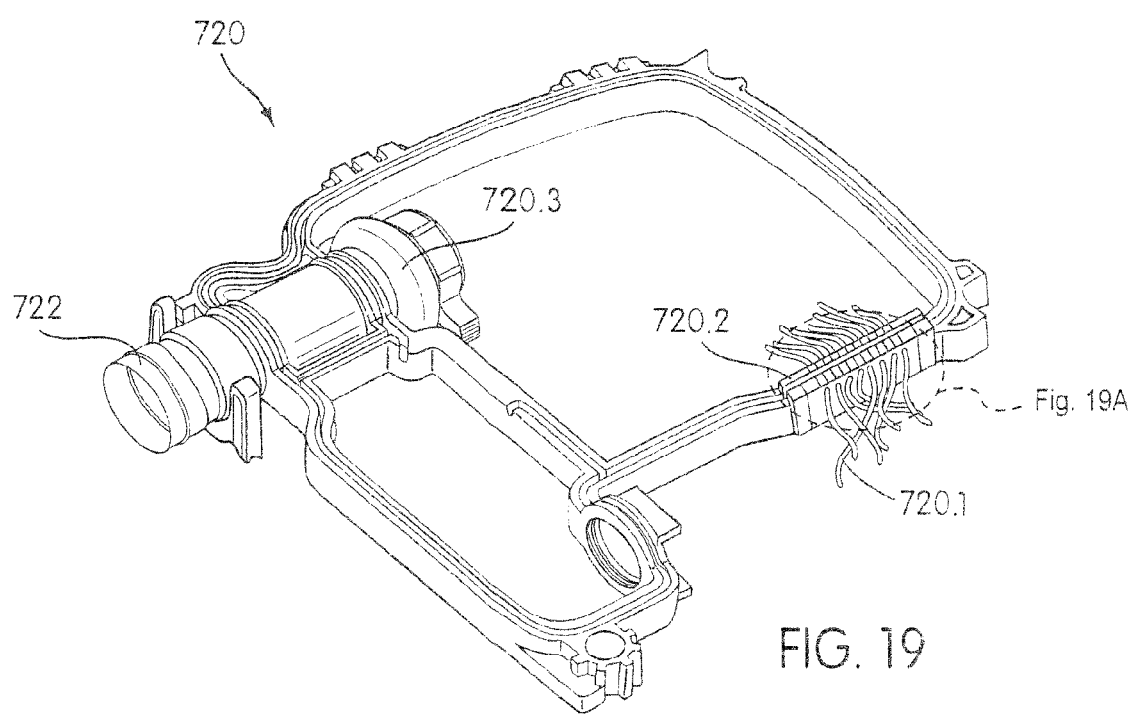
FIG. 19 is a top perspective view of the main seal of the enclosure of FIG. 14.

In one embodiment, the main seal 720 is made from rubber, e.g. silicone rubber. A main seal construed from rubber may aid in reducing noise that can be created by vibrations of enclosure base 710 and enclosure lid 730. Main seal 720 allows for a plurality of blower wires 720.1 to pass therethrough. For example, seal includes a plurality of fingers 720.2 that are resiliently flexible, as shown in FIG. 19A. Adjacent pairs of fingers 720.2 define an aperture, e.g., a round hole, to accommodate the cross-sectional shape of wires 720.1. Main seal 720 also includes a relatively thinner and/or more flexible portion 720.3 to facilitate alignment and coupling with blower outlet. In the illustrated embodiment, the seal gasket includes apertures for allowing the passage of the eight wires that form the blower motor power and control leads. The typically bunched wires would not readily lend themselves to cooperating with a compression silicon gasket in order to achieve the desired sealing. The emergence point of the wires from the enclosure is designed so as not to compromise the enclosure's seal. In this embodiment eight apertures are formed in the seal gasket, each one intended to receive one of the motor wires. Each aperture is in the form of a circular orifice intersected with a 'V' split leading up to the top of the silicone gasket. The 'V' split facilitates the easy locating of the wire into the circular orifice. On assembly of the enclosure, each wire is located in its allocated circular orifice, and the seal is positioned between the two aluminum-casing sections. The force imposed when the screws as tightened cause silicone to fill the space of each circular orifice and around each wire and thereby achieve the seal.

Figure 20:
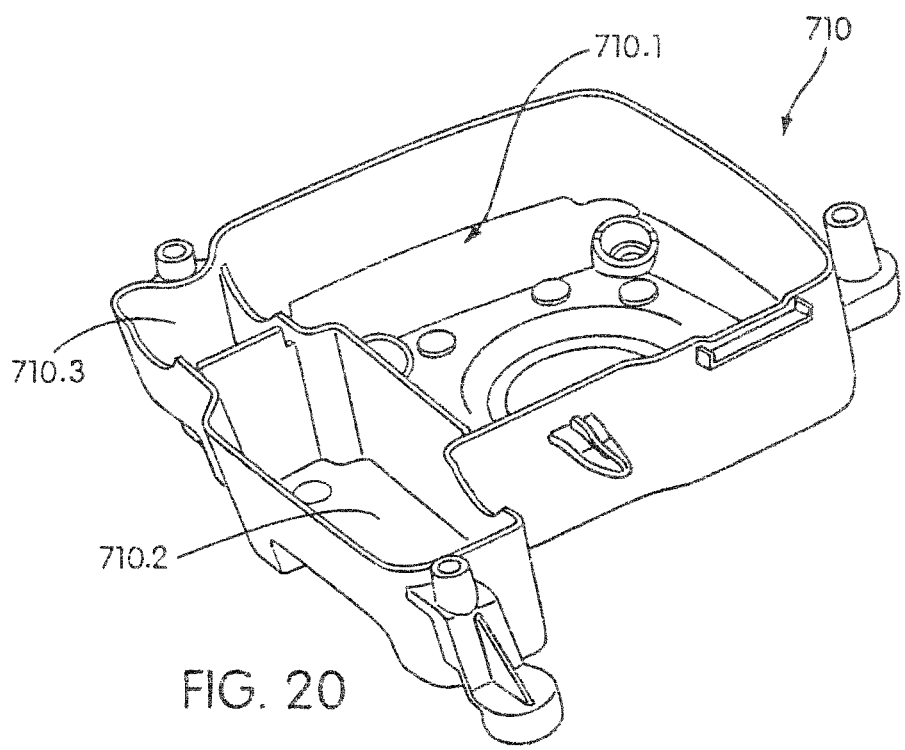
FIG. 20 is a top perspective view of the enclosure base of the enclosure of FIG. 14.
Figure 21:
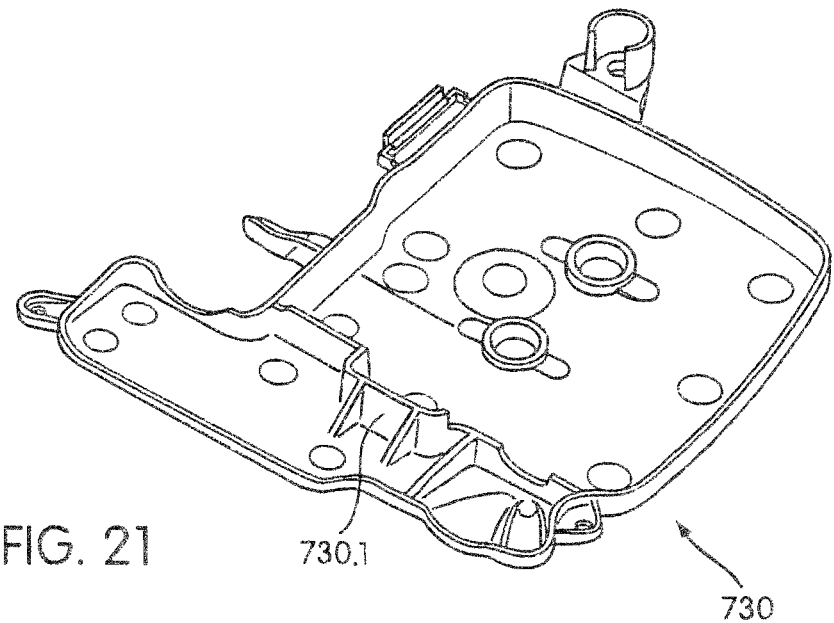
FIG. 21 is a bottom perspective view of the enclosure lid of the enclosure of FIG. 14.

In addition, the main seal 720 aids in minimizing leaks. See also FIG. 20 for an individual representation of the enclosure base 710 and FIG. 21 for an individual representation of enclosure lid 730. As shown in FIG. 20, base 710 includes a blower chamber 710.1 and a muffling chamber 710.2. Base 710 includes a secondary expansion or muffling chamber 710.2 to muffle noise as pressurized gas passes through straight section 722.1 out of outlet 722. Lid 730 includes a channel forming member 730.1 which allows incoming air to travel from muffling chamber 710.1 to blower chamber 710.2. See the directional arrows in FIGS. 15 and 16.

The resulting structure is an enclosure that is completely sealed i.e., has only known, characterized air paths. By contrast, uncharacterized air paths or leaks have undesirable consequences:

A. Inappropriate flow generator performance due to the processing of any inaccurate flow signal. Inappropriate flow generator performance may compromise patient treatment. The control circuit corrects the filtered flow signal to estimate the flow at identified points of the breathing circuit, e.g., at the blower outlet or at the patient interface. The corrected flow signal is used by the treatment algorithm or by other systems such as a flow generator, a fault diagnosis system, etc., and the control circuit responds accordingly. An example of a flow generator fault diagnosis system that can use a corrected flow signal embodied within blowers commercially available from ResMed. The control circuit's performance is dependent upon the flow sensor providing a signal that maintains a known relationship with the downstream flow. The known relationship will not be applicable; or will be less accurate, where the enclosure seal is compromised. Accordingly the corrected flow signal will not be accurate where the enclosure leak is unpredictable in occurrence, in magnitude or otherwise not recognizable as being inaccurate by the control circuit. Therefore to maximize performance of system that places the flow sensor upstream of the blower it is preferable to eliminate the opportunity for the occurrence of unintended leaks in the flow generator.

B. A sealed enclosure will prevent contamination of the breathable gas flowing through the enclosure.

C. A sealed enclosure will prevent the breathable gas escaping from the air path. This is a particularly desirable when oxygen or other treatment gas is added to the flow through the flow generator.

D. A sealed enclosure will maximize the effect of the enclosure's noise attenuating characteristics.

The silicone pathway connected to the blower outlet is preferably molded in one piece with the seal. This configuration means that there is no need for the sealing gasket to assume the shape and degree of precision that would otherwise be required to property fit around an enclosed rigid outlet pipe or to achieve a seal should the rigid outlet pipe be formed of two or more separable parts.

Figure 22A:
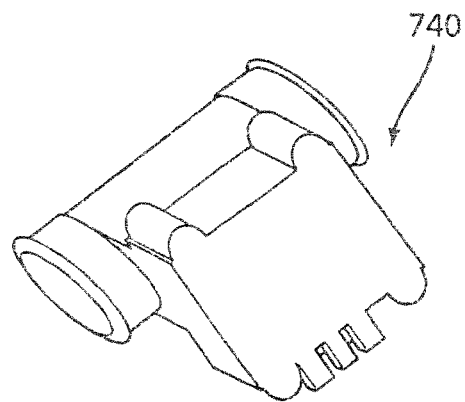
FIGS. 22A and 22B are perspective views of the flow meter of the enclosure of FIG. 14.
Figure 22B:
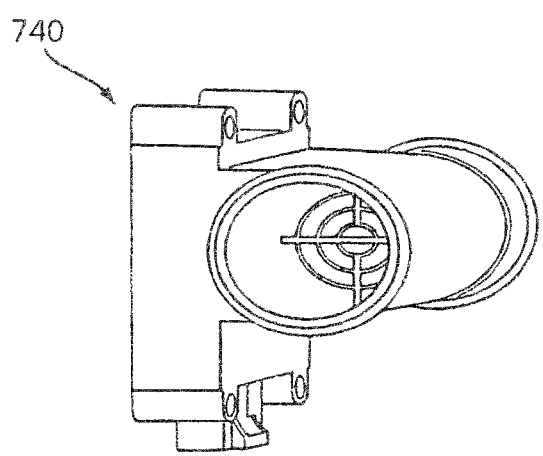

A flow meter 740 is sealingly connected to main seal 720. See also FIGS. 22A and 22B for an individual representation of a flow meter. In one embodiment, the flow meter is designed to measure air flows in the range of 0-200 LPM, and preferably in the range of 150-180 LPM. In a further embodiment, the flow meter is designed to be safe for even 100% oxygen flows. As evident from FIGS. 14-17, the flow meter may be positioned upstream from the blower inlet. Positioning the flow meter upstream instead of downstream can be helpful in improving the accuracy of air flow measurement as it reduces/minimizes blower-induced turbulence in the air presented to the flow meter. This, in turn, provides an improved signal to the control algorithm, which signal does not require complex filtering of turbulence or noise to provide a useful signal.

Figure 23:
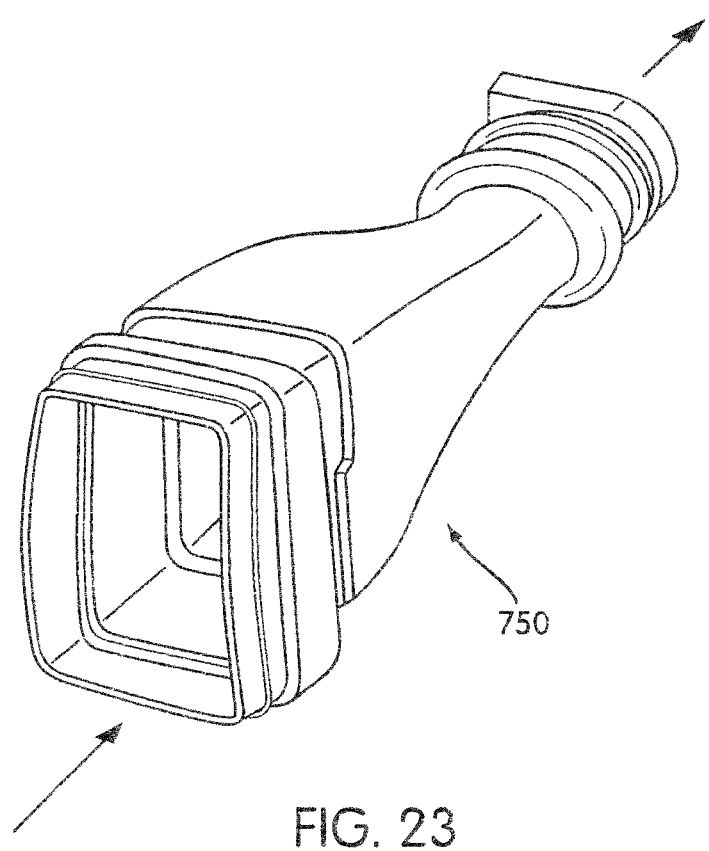
FIG. 23 is a perspective view of the inlet connector of the enclosure of FIG. 14.

An inlet connector 750 is sealingly connected to flow meter 740. The inlet connector ensures that the air intake is supplied from outside the flow generator. See also FIG. 23 for an individual representation of the inlet connector. In one embodiment, the inlet connector is made from plastic and/or rubber, e.g. silicone rubber. The inlet connector 750 provides location for filter retainer 755. See FIG. 24. The filter retainer 755 can be sealingly inserted in the opening 752 of the inlet connector 750 and serves to receive a filter. For example, filter retainer includes a flange 755.1 that is received within a groove 750.1 of the inlet connector 750, upon assembly. In accordance with the depicted embodiment, the filter retainer 755 may be construed asymmetrically to conveniently and safely give a user only one correct way of placing the filter. Furthermore, the filter retainer 755 prevents the inlet connector 750 from sagging. Filter retainer 755 also includes one or more cross bars 755.2 that prevent the filter from being sucked into the inlet connector 750. Filter retainer 755 also includes a pair of receiving apertures 755.3 to receive an inlet cap with resilient arms.

Also, the inlet connector 750 provides a barrier for water being able to reach the blower. First, in combination with the filter retainer 755 and filter cover (not shown) it forms a water barrier at the entry of the enclosure. Second, with the enclosure being positioned horizontal, the upward slope 753 of the inlet connector (See FIG. 17) provides an obstacle for water being spilled into the inlet connector 750 to travel further into the system.

Further, inlet connector 750 provides a relatively linear flow of air to flow meter 740, which helps decrease turbulence and the creation of "noise" that would otherwise need to be filtered before providing a useful signal to the control algorithm. Moreover, there is no need to maintain a linear path downstream of the flow meter 740, which opens further design options.

The illustrated embodiments utilize this freedom of configuration by placing the flow sensor generally parallel with blower. This configuration reduces the overall length of the flow generator as it allows for the desired linear (i.e., turbulence minimizing) pathway between the flow generator air-from-atmosphere inlet and the flow sensor inlet while eliminating the length adding placement of the flow sensor and connecting turbulence-reducing linear pathway at the blower outlet. This configuration has the air travel around a corner (i.e., a typically turbulence inducing maneuver) into muffler chamber which is situated forward of the blower chamber. From there the air enters the blower chamber and then enters the blower inlet. The turbulent air emerging from the blower outlet travels a short distance through a silicone pathway to the flow generator outlet. The linear component connecting the flow generator air-from-atmosphere inlet to the flow sensor inlet may be conveniently located in any position relative to the blower because of the irrelevance of avoiding the development of turbulence after the flow sensor outlet. Furthermore there is avoided the need to perform flow signal filtering to eliminate the remnant blower-induced turbulence.

Each of the described embodiments provides for a modular construction having relatively few, self-aligning components that may be readily assembled and disassembled for maintenance. The inner sides of the aluminum-casing sections include locating feature buckets to facilitate the positioning and retention of internal components such as the blower suspension springs, or alternatively, substitute silicone suspension bushes.

Another feature relates to a safety measure. If motor bearing wear reaches a predetermined limit, the consequent shaft movement will position a shaft mounted blade so as to cut something on or protruding from the motor internal circuit board and thereby cause the motor to stop (say due to a loss of power). The amount of shaft movement required to give effect to this would be something less than the amount of movement required to have the shaft mounted impeller make contact with the volute wall. In this way the system stops before impeller/volute wall scraping or collision would lead to denegation of either or both components and cause particles to contaminate the air path or friction that would cause ignition to occur—especially in an oxygen rich environment (i.e., where oxygen is being added to the breathing gas).

While the invention has been described by way of example embodiments, it is understood that the words which have been used herein are words of description, rather than words of limitation. Changes may be made without departing from the scope and spirit of the invention in its broader aspects. Although the invention has been described herein with reference to particular embodiments, it is understood that the invention is not limited to the particulars disclosed. The invention extends to all appropriate equivalent structures, uses and mechanisms.

What is claimed is:

1. An enclosure for a blower configured to generate a positive pressure flow of gas, the enclosure comprising:
 a base defining a plurality of chambers;
 a lid that engages the base to enclose the plurality of chambers; and
 a seal sandwiched between the base and the lid so that the enclosure defines a substantially closed air path, the seal defining an outlet conduit adapted to direct pressurized gas out of the enclosure.

2. An enclosure according to claim 1, wherein the plurality of chambers comprise a blower chamber adapted to receive the blower and a muffling chamber positioned upstream of the blower chamber.

3. An enclosure according to claim 2, wherein the plurality of chambers are divided by an interior wall, a lower portion of the wall being defined by the base and an upper portion of the wall being defined by the seal.

4. An enclosure according to claim 3, wherein the seal defines an inlet adapted to receive an outlet of a flow meter.

5. An enclosure according to claim 4, wherein a portion of the seal comprises a gasket.

6. An enclosure according to claim 1, wherein at least a portion of the outlet conduit is formed integrally with the seal.

7. An enclosure according to claim 1, wherein the outlet conduit is removable from the base with the seal.

8. An enclosure according to claim 1, wherein the seal, the base and the lid together form the substantially closed air path.

9. An enclosure according to claim 1, wherein at least a portion of the outlet conduit is an extension of the seal.

10. A blower assembly comprising:
a blower configured to generate a positive pressure flow of gas;
the enclosure of claim 2; and
a flow meter positioned upstream of the muffling chamber,
wherein the seal defines an inlet adapted to receive an outlet of a flow meter.

11. A blower assembly according to claim 10, wherein the muffling chamber is connected to a flow meter outlet via the inlet defined by the seal.

12. A blower assembly according to claim 11, further comprising an inlet connector that is in communication with atmospheric air and is connected to an inlet side of the flow meter.

13. A blower assembly according to claim 12, wherein the inlet connector defines a substantially linear path from atmosphere to the flow meter.

14. An enclosure for a blower configured to generate a positive pressure flow of gas, the enclosure comprising:
a base with an interior wall dividing an interior space of the enclosure into a first chamber and a second chamber;
a lid that engages the base to enclose the interior space; and
a seal sandwiched between the base and the lid so as to define a substantially closed air path, the seal including an interior wall sandwiched between the lid and the interior wall of the base,
wherein the seal defines an air path inlet into the enclosure and defines an air path outlet out of the enclosure.

15. An enclosure according to claim 14, wherein a first portion of the seal is a gasket and a second portion of the seal defines an outlet conduit adapted to direct pressurized gas out of the enclosure.

16. An enclosure according to claim 15, wherein the gasket portion of the seal comprises a plurality of apertures configured to receive wiring from the blower, the apertures extending from the interior space of the enclosure to an exterior of the enclosure.

17. A blower assembly comprising:
a blower configured to generate a positive pressure flow of gas;
the enclosure of claim 14;
a flow meter positioned upstream of the enclosure; and
an inlet connector upstream of the flow meter and in communication with a gas source.

18. A blower assembly according to claim 17, wherein the inlet connector defines a substantially linear air path that flows in a direction substantially parallel to a side of the enclosure base closest to the inlet connector.

19. A blower assembly according to claim 18, wherein the inlet connector is oriented to slope downward toward the flow meter when the blower assembly is in an upright operating position.

20. A blower assembly according to claim 16, wherein the inlet connector comprises a filter retainer configured to retain a filter cover that forms a water barrier at an entry of the inlet connector.

21. An enclosure for a blower configured to generate a positive pressure flow of gas, the enclosure comprising:
a base;
a lid that engages the base to enclose an interior space that is divided into a blower chamber and a muffling chamber; and
a seal sandwiched between the base and the lid so as to define a substantially closed air path,
wherein the seal cooperates with the base and the lid to define the blower chamber and the muffling chamber, and
wherein the seal defines an enclosure inlet and an enclosure outlet.

22. An enclosure according to claim 21, wherein the blower chamber is adapted to receive the blower and the muffling chamber is adapted to dampen vibration caused by turbulence upstream of the blower chamber.

23. An enclosure according to claim 22, wherein a first portion of the seal comprises a gasket sandwiched between edges of the lid and the base, and a second portion of the seal comprises an outlet conduit adapted to be connected to an outlet of the blower and direct pressurized gas from the blower out of the enclosure.

24. A blower assembly comprising:
a blower configured to generate a positive pressure flow of gas;
the enclosure of claim 21;
a flow meter positioned upstream of the enclosure; and
an inlet connector upstream of the flow meter and in communication with a gas source.

25. A blower assembly according to claim 24, wherein a first airflow path upstream of the flow meter is substantially linear and a second airflow path downstream of the flow meter is non-linear.

26. A blower assembly according to claim 25, wherein the blower engages the base and the lid of the enclosure through vibration dampening members.

27. A blower assembly according to claim 26, wherein the vibration dampening members are springs.

28. A blower assembly according to claim 26, wherein the vibration dampening members are suspension bushes.

* * * * *